US006251392B1

(12) United States Patent
Hein et al.

(10) Patent No.: US 6,251,392 B1
(45) Date of Patent: *Jun. 26, 2001

(54) EPITHELIAL CELL TARGETING AGENT

(75) Inventors: Mich B. Hein, Fallbrook; Andrew C. Hiatt, San Diego; John H. Fitchen, La Jolla, all of CA (US)

(73) Assignee: Epicyte Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/954,211

(22) Filed: Oct. 20, 1997

(51) Int. Cl.$^7$ .......................... A61K 39/395; C12N 9/96; C07K 16/00
(52) U.S. Cl. .................. 424/134.1; 435/188; 424/143.1; 424/172.1; 424/174.1; 424/182.1; 424/183.1; 530/861; 530/863; 530/387.1
(58) Field of Search ...................................... 530/861, 863, 530/864, 865, 866, 391.5, 391.7, 391.9, 387.1; 435/188, 188.5, 195, 219; 424/179.1, 180.1, 181.1, 183.1, 134.1, 138.1, 143.1, 182.1, 172.1, 174.1

(56) References Cited

U.S. PATENT DOCUMENTS

| 5,055,291 | * | 10/1991 | Lam et al. . |
| 5,169,627 | | 12/1992 | Cunningham-Rundles . |
| 5,202,422 | | 4/1993 | Hiatt et al. . |
| 5,208,020 | * | 5/1993 | Chari et al. . |
| 5,284,931 | | 2/1994 | Springer et al. . |
| 5,597,569 | * | 1/1997 | Siegall et al. . |
| 5,639,947 | | 6/1997 | Hiatt et al. . |
| 5,670,626 | | 9/1997 | Chang . |
| 5,683,694 | * | 11/1997 | Bagshawe et al. . |

FOREIGN PATENT DOCUMENTS

| 58-134032 | 8/1983 | (JP) . |
| WO 98/30591 | 7/1998 | (WO) . |
| WO 98/30592 | 7/1998 | (WO) . |

OTHER PUBLICATIONS

Paul, W.E. Fundamental Immunology, Raven Press, New York, pp. 132–133, 1984.*
Ferkol et al., "Gene Transfer into Respiratory Epithelial Cells by Targeting the Polymeric Immunoglobulin Receptor," *J. Clin. Invest.* 92: 2394–2400, 1993.
Terskikh et al., "Dimeric Recombinant IgA Directed Against Carcino–Embryonic Antigen, A Novel Tool For Carcinoma Localization," *Molecular Immunology* 31(17): 1313–1319, 1994.
Hendrickson et al., "Altered Hepatic Transport of Immunoglublin A in Mice Lacking the J Chain," *J. Exp. Med.* 182: 1905–1911, 1995.
Max and Korsmeyer, "Human J Chain Gene. Structure and Expression in B Lymphoid Cells," *Journal of Experimental Medicine* 161: 832–849, 1985.
Frutiger et al., "Disulfide Bond Assignment in Human J Chain and Its Covalent Pairing with Immunoglobulin M," *Biochemistry* 31: 12643–12647, 1992.
Kulseth and Rogne, "Cloning and Characterization of the Bovine Immunoglobulin J Chain cDNA and Its Promoter Region," *DNA and Cell Biology* 13: 37–42, 1994.
Rifai and Mannik, "Clearance Kinetics and Fate of Mouse IgA Immune Complexes Prepared with Monomeric or Dimeric IgA," *Journal of Immunology* 130(4): 1826–1832, 1983.
Burns et al., "Protective Effect of Ratavirus VP6–Specific IgA Monoclonal Antibodies That Lack Neutralizing Activity," *Science* 272: 104–107, 1996.
Mazanec et al., "Intracellular Neutralization of Influenza Virus by Immunoglobulin A Anti–Hemagglutinin Monoclonal Antibodies," *Journal of Virology* 69(2): 1339–1343, 1995.
Kaetzel et al., "The polymeric immunoglobin receptor (secretory components) mediates transport of immune complexes across epithelial cells: A Local defense function for IgA," *Proc. Natl. Acad. Sci.* 88:8796–8800, 1991.
Kaetzel et al., "Epithelial Transcytosis of Monomeric IgA and IgG Cross–linked Through Antigen to Polymeric IgA. A Role for Monomeric Antibodies in the Mucosal Immune System," *Journal of Immunology* 152: 72–76, 1994.
Sheldrake et al., "Selective Transport of Serum–Derived IgA Into Mucosal Secretions," *Journal of Immunology* 132(1): 363–368, 1984.
Mestecky et al., "The Role of the Liver in Catabolism of Mouse and Human IgA," *Immunological Investigations* 18(1–4): 313–324, 1989.
Youngman et al., "Inhibition of IFN–γ Activity in Supernatants from Stimulated Human Intestinal Mononuclear Cells Prevents Up–Regulation of the Polymeric Ig Receptor in an Intestinal Epithelial Cell Line," *Journal of Immunology* 153: 675–681, 1994.
Rifai et al., "Clearance Kinetics and Fate of Macromolecular IgA in Patients with IgA Nephropathy," *Laboratory Investigation* 61(4): 381–388, 1989.
Emancipator and Lamm, "IgA Nephropathy: Overproduction on Decreased Clearance of Immune Complexes?" *Laboratory Investigation* 61(4): 365–367, 1989.
Nagura et al., "Translocation of Dimeric IgA Through Neoplastic Colon Cells In Vitro," *Journal of Immunology* 123(5): 2359–2368, 1979.
Mannik and Arend, "Fate of Preformed Immune Complexes in Rabbits and Rhesus Monkeys," *Journal of Experimental Medicine* 134(3 pt. 2): 19s–31s, 1971.

(List continued on next page.)

Primary Examiner—Anthony C. Caputa
Assistant Examiner—Anne L. Holleran
(74) Attorney, Agent, or Firm—Seed Intellectual Property Law Group LLC

(57) ABSTRACT

Targeting molecules for use in delivering biological agents to non-polarized epithelial cells are disclosed. Upon delivery, the biological agent(s) are lethal to the epithelial cell. The targeting molecules may be used, for example, for the eradication of metastatic epithelial cells.

3 Claims, 1 Drawing Sheet

OTHER PUBLICATIONS

Brown and Koshland, "Evidence for a long–ranged conformational change induced by antigen binding to IgM antibody," *Proc. Natl. Acad. Sci. USA* 74(12): 5682–5686, 1977.

Brandtzaef and Baklien, "Immunohistochemical studies of the immunoglobulin–producing cell systems of the human intestinal mucosa," *Acta Histochemica Suppl.* 21: 105–119, 1980.

Allen et al., "An immunoperoxidase study of epithelial marker antigens in ulcerative colitis with dysplasia and carcinoma," *J. Clin. Pathol.* 38: 18–29, 1985.

Wells, "Additivity of Mutational Effects in Proteins," *Biochemistry* 29(37): 8509–8517, 1990.

Verma and Somia, "Gene therapy—promises, problems and prospects," *Nature* 389: 239–242, 1997.

Brandtzaeg et al., "Direct evidence for an integrated function of J chain and secretory component in epithelial transport of immunoglobulins," *Nature* 311: 71–73, 1984.

Natvig et al., "Mechanism for Enhanced External Transfer of Dimeric IgA over Pentameric IgM," *The Journal of Immunology* 159: 4330–4340, 1997.

Vaerman et al., "Lack of SC/pIgR–mediated epithelial transport of a human polymeric IgA devoid of J chain: in vitro and in vivo studies," *Immunology* 95: 90–96, 1998.

\* cited by examiner

SEQUENCE COMPARISON OF J CHAIN PROTEINS AND DEDUCED J CHAIN SEQUENCES FROM SIX ORGANISMS

```
          10        20        30        40        50        60
 -1--------X---------X---------X---------X---------X---------X
QEDERIVLVDNKCKCARITSRIIRSSEDPNEDIVERNIRIIVPLNNRENISDPTSPLRTRF
-DENERIV--------------P-A---SQ------V-------S----------M--K-
D--ATI-A----M-T-V-----P-T--------------V----------------RN-
---ST-------Q-V--------DPDN-S---------------T------------E-
  EQEYI-AN-----VK-S--FVP-T-R-G-E-L----Q-TI-TSS-MX----Y-----Q-
         ---M-T-V-A--RGTR---------Y---N---K--G----------NQ- 70        80        90       100       110       120
----------X---------X---------X---------X---------X---------X
VYHLSDLCKKCDPTEVELDNQIVTATQSNICDEDSAT ETCYTY    DRNKCYTAVVPL
-------------T------ED-V---S------S-A  ------   -------NR-K-
------V------V----ED-V----------N--DGVP----M-   -------TM---
K-N-AN----------I-----VF--S-----PD-DYS ------   -------TL--I
--N-W-I-Q----VQL-IGGIP-L-S-PXXSKP-dE             ---TE-NF
-----PS------   YEDGV----ET---YP-QGVPQS-RD-CPEL-------VL--P 130       140
----------X---------X---------X---
VYGGETKMVETALTPDACYPD      HUMAN
S-R-Q-----------S----      BOVINE
R-H------QA-----S----      MOUSE
THR-V-R--KAT----S----      RABBIT
K        KKVP----S--EYSE   BULL FROG
G-T------QN----------      EARTH WORM
```

*Fig. 1*

```
                            SEQUENCE LISTING (1) GENERAL INFORMATION:

(iii) NUMBER OF SEQUENCES: 89

(2) INFORMATION FOR SEQ ID NO: 1:

(i) SEQUENCE CHARACTERISTICS:
        (A) LENGTH: 137 amino acids
        (B) TYPE: amino acid
        (C) STRANDEDNESS:
        (D) TOPOLOGY: linear (xi) SEQUENCE DESCRIPTION: SEQ ID NO: 1:

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Pro Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
```

```
           130                 135

(2) INFORMATION FOR SEQ ID NO: 2:

(i) SEQUENCE CHARACTERISTICS:
        (A) LENGTH: 135 amino acids
        (B) TYPE: amino acid
        (C) STRANDEDNESS:
        (D) TOPOLOGY: linear (xi) SEQUENCE DESCRIPTION: SEQ ID NO: 2:

Gln Asp Glu Asn Glu Arg Ile Val Val Asp Asn Lys Cys Lys Cys Ala
1               5                   10                  15

Arg Ile Thr Ser Arg Ile Ile Pro Ser Ala Glu Asp Pro Ser Gln Asp
            20                  25                  30

Ile Val Glu Arg Asn Val Arg Ile Ile Val Pro Leu Asn Ser Arg Glu
        35                  40                  45

Asn Ile Ser Asp Pro Thr Ser Pro Met Arg Thr Lys Pro Val Tyr His
    50                  55                  60

Leu Ser Asp Leu Cys Lys Lys Cys Asp Thr Thr Glu Val Glu Leu Glu
65                  70                  75                  80

Asp Gln Val Val Thr Ala Ser Gln Ser Asn Ile Cys Asp Ser Asp Ala
                85                  90                  95

Glu Thr Cys Tyr Thr Tyr Asp Arg Asn Lys Cys Tyr Thr Asn Arg Val
            100                 105                 110

Lys Leu Ser Tyr Arg Gly Gln Thr Lys Met Val Glu Thr Ala Leu Thr
            115                 120                 125

Pro Asp Ser Cys Tyr Pro Asp
    130                 135

(2) INFORMATION FOR SEQ ID NO: 3:

(i) SEQUENCE CHARACTERISTICS:
        (A) LENGTH: 137 amino acids
        (B) TYPE: amino acid
        (C) STRANDEDNESS:
        (D) TOPOLOGY: linear (xi) SEQUENCE DESCRIPTION: SEQ ID NO: 3:

Asp Asp Glu Ala Thr Ile Leu Ala Asp Asn Lys Cys Met Cys Thr Arg
1               5                   10                  15

Val Thr Ser Arg Ile Ile Pro Ser Thr Glu Asp Pro Asn Glu Asp Ile
            20                  25                  30

Val Glu Arg Asn Ile Arg Ile Val Val Pro Leu Asn Asn Arg Glu Asn
        35                  40                  45

Ile Ser Asp Pro Thr Ser Pro Leu Arg Arg Asn Pro Val Tyr His Leu
    50                  55                  60

Ser Asp Val Cys Lys Lys Cys Asp Pro Val Glu Val Glu Leu Glu Asp
65                  70                  75                  80

Gln Val Val Thr Ala Thr Gln Ser Asn Ile Cys Asn Glu Asp Asp Gly
                85                  90                  95

Val Pro Glu Thr Cys Tyr Met Tyr Asp Arg Asn Lys Cys Tyr Thr Thr
            100                 105                 110

Met Val Pro Leu Arg Tyr His Gly Glu Thr Lys Met Val Gln Ala Ala
            115                 120                 125

Leu Thr Pro Asp Ser Cys Tyr Pro Asp
        130                 135
```

(2) INFORMATION FOR SEQ ID NO: 4:

(i) SEQUENCE CHARACTERISTICS:
        (A) LENGTH: 136 amino acids
        (B) TYPE: amino acid
        (C) STRANDEDNESS:
        (D) TOPOLOGY: linear (xi) SEQUENCE DESCRIPTION: SEQ ID NO: 4:

```
Glu Asp Glu Ser Thr Val Leu Val Asp Asn Lys Cys Gln Cys Val Arg
1               5                   10                  15

Ile Thr Ser Arg Ile Ile Arg Asp Pro Asp Asn Pro Ser Glu Asp Ile
            20                  25                  30

Val Glu Arg Asn Ile Arg Ile Ile Val Pro Leu Asn Thr Arg Glu Asn
        35                  40                  45

Ile Ser Asp Pro Thr Ser Pro Leu Arg Thr Glu Pro Lys Tyr Asn Leu
50                  55                  60

Ala Asn Leu Cys Lys Lys Cys Asp Pro Thr Glu Ile Glu Leu Asp Asn
65                  70                  75                  80

Gln Val Phe Thr Ala Ser Gln Ser Asn Ile Cys Pro Asp Asp Asp Tyr
                85                  90                  95

Ser Glu Thr Cys Tyr Thr Tyr Asp Arg Asn Lys Cys Tyr Thr Thr Leu
            100                 105                 110

Val Pro Ile Thr His Arg Gly Val Thr Arg Met Val Lys Ala Thr Leu
        115                 120                 125

Thr Pro Asp Ser Cys Tyr Pro Asp
130                 135
```

(2) INFORMATION FOR SEQ ID NO: 5:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO: 5:

```
Glu Gln Glu Tyr Ile Leu Ala Asn Asn Lys Cys Lys Cys Val Lys Ile
1               5                   10                  15

Ser Ser Arg Phe Val Pro Ser Thr Glu Arg Pro Gly Glu Glu Ile Leu
            20                  25                  30

Glu Arg Asn Ile Gln Ile Thr Ile Pro Thr Ser Ser Arg Met Xaa Ile
        35                  40                  45

Ser Asp Pro Tyr Ser Pro Leu Arg Thr Gln Pro Val Tyr Asn Leu Trp
50                  55                  60

Asp Ile Cys Gln Lys Cys Asp Pro Val Gln Leu Glu Ile Gly Gly Ile
65                  70                  75                  80

Pro Val Leu Ala Ser Gln Pro Xaa Xaa Ser Xaa Pro Asp Asp Glu Cys
                85                  90                  95

Tyr Thr Thr Glu Val Asn Phe Lys Lys Lys Val Pro Leu Thr Pro Asp
            100                 105                 110

Ser Cys Tyr Glu Tyr Ser Glu
        115
```

(2) INFORMATION FOR SEQ ID NO: 6:

(i) SEQUENCE CHARACTERISTICS:
        (A) LENGTH: 128 amino acids
        (B) TYPE: amino acid
        (C) STRANDEDNESS:

(D) TOPOLOGY: linear (xi) SEQUENCE DESCRIPTION: SEQ ID NO: 6:

| | | | | | | | | | | | | | | |
|---|---|---|---|---|---|---|---|---|---|---|---|---|---|---|
| Asn | Lys | Cys | Met | Cys | Thr | Arg | Val | Thr | Ala | Arg | Ile | Arg | Gly | Thr | Arg |
| 1 | | | | 5 | | | | | 10 | | | | | 15 | |

| Glu | Asp | Pro | Asn | Glu | Asp | Ile | Val | Glu | Arg | Tyr | Ile | Arg | Ile | Asn | Val |
|---|---|---|---|---|---|---|---|---|---|---|---|---|---|---|---|
| | | | 20 | | | | | 25 | | | | | 30 | | |

| Pro | Leu | Lys | Asn | Arg | Gly | Asn | Ile | Ser | Asp | Pro | Thr | Ser | Pro | Leu | Arg |
|---|---|---|---|---|---|---|---|---|---|---|---|---|---|---|---|
| | | 35 | | | | | 40 | | | | | 45 | | | |

| Asn | Gln | Pro | Val | Tyr | His | Leu | Ser | Pro | Ser | Cys | Lys | Lys | Cys | Asp | Pro |
|---|---|---|---|---|---|---|---|---|---|---|---|---|---|---|---|
| | 50 | | | | | 55 | | | | | 60 | | | | |

| Tyr | Glu | Asp | Gly | Val | Val | Thr | Ala | Thr | Glu | Thr | Asn | Ile | Cys | Tyr | Pro |
|---|---|---|---|---|---|---|---|---|---|---|---|---|---|---|---|
| 65 | | | | | 70 | | | | | 75 | | | | | 80 |

| Asp | Gln | Gly | Val | Pro | Gln | Ser | Cys | Arg | Asp | Tyr | Cys | Pro | Glu | Leu | Asp |
|---|---|---|---|---|---|---|---|---|---|---|---|---|---|---|---|
| | | | | 85 | | | | | 90 | | | | | 95 | |

| Arg | Asn | Lys | Cys | Tyr | Thr | Val | Leu | Val | Pro | Pro | Gly | Tyr | Thr | Gly | Glu |
|---|---|---|---|---|---|---|---|---|---|---|---|---|---|---|---|
| | | | 100 | | | | | 105 | | | | | 110 | | |

| Thr | Lys | Met | Val | Gln | Asn | Ala | Leu | Thr | Pro | Asp | Ala | Cys | Tyr | Pro | Asp |
|---|---|---|---|---|---|---|---|---|---|---|---|---|---|---|---|
| | | 115 | | | | | 120 | | | | | 125 | | | |

(2) INFORMATION FOR SEQ ID NO: 7:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..414

(xi) SEQUENCE DESCRIPTION: SEQ ID NO: 7:

```
GAT CAG GAA GAT GAA CGT ATT GTT CTG GTT GAC AAC AAG TGC AAG TGT        48
Asp Gln Glu Asp Glu Arg Ile Val Leu Val Asp Asn Lys Cys Lys Cys
 1               5                  10                  15

GCT CGT ATT ACT TCT AGA ATC ATC CGT AGC TCA GAG GAC CCA AAT GAA        96
Ala Arg Ile Thr Ser Arg Ile Ile Arg Ser Ser Glu Asp Pro Asn Glu
                20                  25                  30

GAT ATA GTC GAA CGT AAC ATC CGT ATC ATC GTC CCA CTG AAT AAC CGG       144
Asp Ile Val Glu Arg Asn Ile Arg Ile Ile Val Pro Leu Asn Asn Arg
            35                  40                  45

GAG AAT ATC TCA GAT CCT ACA AGT CCG TTG CGC ACA CGC TTC GTA TAC       192
Glu Asn Ile Ser Asp Pro Thr Ser Pro Leu Arg Thr Arg Phe Val Tyr
        50                  55                  60

CAC CTG TCA GAT CTG TGT AAG AAG TGT GAT CCA ACA GAG GTA GAG CTG       240
His Leu Ser Asp Leu Cys Lys Lys Cys Asp Pro Thr Glu Val Glu Leu
 65                  70                  75                  80

GAC AAT CAG ATA GTC ACT GCG ACT CAA AGC AAC ATT TGC GAT GAG GAC       288
Asp Asn Gln Ile Val Thr Ala Thr Gln Ser Asn Ile Cys Asp Glu Asp
                85                  90                  95

AGC GCT ACA GAA ACC TGC AGC ACC TAC GAT AGG AAC AAA TGC TAC ACG       336
Ser Ala Thr Glu Thr Cys Ser Thr Tyr Asp Arg Asn Lys Cys Tyr Thr
            100                 105                 110

GCC GTG GTT CCG CTC GTG TAT GGT GGA GAG ACA AAA ATG GTG GAA ACT       384
Ala Val Val Pro Leu Val Tyr Gly Gly Glu Thr Lys Met Val Glu Thr
        115                 120                 125

GCC CTT ACG CCC GAT GCA TGC TAT CCG GAC TGAATTC                        421
Ala Leu Thr Pro Asp Ala Cys Tyr Pro Asp
130                 135
```

(2) INFORMATION FOR SEQ ID NO: 8:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..213

(xi) SEQUENCE DESCRIPTION: SEQ ID NO: 8:

```
GAT CAG AAG TGC AAG TGT GCT CGT ATT ACT TCT AGA ATC ATC CGT AGC        48
Asp Gln Lys Cys Lys Cys Ala Arg Ile Thr Ser Arg Ile Ile Arg Ser
 1               5                  10                  15

TCA GAG GAC CCA AAT GAA GAT ATA GTC GAA CGT AAC ATC CGT ATC ATC        96
Ser Glu Asp Pro Asn Glu Asp Ile Val Glu Arg Asn Ile Arg Ile Ile
             20                  25                  30

GTC CCA CTG AAT AAC CGG GAG AAT ATC TCA GAT CCT ACA AGT CCG TTG       144
Val Pro Leu Asn Asn Arg Glu Asn Ile Ser Asp Pro Thr Ser Pro Leu
         35                  40                  45

CGC ACA CGC TTC GTA TAC CAC CTG TCA GAT CTG TGT AAG AAG GAT GAG       192
Arg Thr Arg Phe Val Tyr His Leu Ser Asp Leu Cys Lys Lys Asp Glu
     50                  55                  60

GAC AGC GCT ACA GAA ACC TGC TG                                        215
Asp Ser Ala Thr Glu Thr Cys
 65                  70
```

(2) INFORMATION FOR SEQ ID NO: 9:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO: 9:

```
CTAGAATCAT CCGTAGCTCA GAGGACCCAA ATGAAGATAT AGTCGAACGT AACATCCGTA      60

TCATCGTCCC ACTGAATAAC CGGGAGAATA TCTCAGATCC TACAAGTCCG TTGCGCACAC     120

GCTTCGTATA CCACCTGTCA                                                 140
```

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 10:

```
GATCAGAAGT GCAAGTGTGC TCGTATTACT T                                     31
```

(2) INFORMATION FOR SEQ ID NO: 11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..42

(xi) SEQUENCE DESCRIPTION: SEQ ID NO: 11:

```
GAT CTG TGT AAG AAG GAT GAA GAT TCC GCT ACA GAA ACC TGC          42
Asp Leu Cys Lys Lys Asp Glu Asp Ser Ala Thr Glu Thr Cys
            75                  80                  85

TG                                                                44
```

(2) INFORMATION FOR SEQ ID NO: 12:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCACCTACGA TAGGAACAAA TGCTACACGG CCGTGGTTCC GCTCGTGTAT GGTGGAGAGA     60

CAAAAATGGT GGAAACTGCC CTTACGCCCG ATGCATGCTA CCCTGACTG               109
```

(2) INFORMATION FOR SEQ ID NO: 13:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..282

(xi) SEQUENCE DESCRIPTION: SEQ ID NO: 13:

```
GAC AAC AAG TGC AAG TGT GCT CGT ATT ACT TCT AGA ATC ATC CGT AGC          48
Asp Asn Lys Cys Lys Cys Ala Arg Ile Thr Ser Arg Ile Ile Arg Ser
 15                  20                  25                  30

TCA GAG GAC CCA AAT GAA GAT ATA GTC GAA CGT AAC ATC CGT ATC ATC          96
Ser Glu Asp Pro Asn Glu Asp Ile Val Glu Arg Asn Ile Arg Ile Ile
                 35                  40                  45

GTC CCA CTG AAT AAC CGG GAG AAT ATC TCA GAT CCT ACA AGT CCG TTG         144
Val Pro Leu Asn Asn Arg Glu Asn Ile Ser Asp Pro Thr Ser Pro Leu
             50                  55                  60

CGC ACA CGC TTC GTA TAC CAC CTG TCA GAT CTG TGT AAG AAG TGT GAT         192
Arg Thr Arg Phe Val Tyr His Leu Ser Asp Leu Cys Lys Lys Cys Asp
         65                  70                  75

CCA ACA GAG GTA GAG CTG GAC AAT CAG ATA GTC ACT GCG ACT CAA AGC         240
Pro Thr Glu Val Glu Leu Asp Asn Gln Ile Val Thr Ala Thr Gln Ser
     80                  85                  90

AAC ATT TGC GAT GAG GAC AGC GCT ACA GAA ACC TGC TAC TGA                 282
Asn Ile Cys Asp Glu Asp Ser Ala Thr Glu Thr Cys Tyr  *
 95                 100                 105

ATTC                                                                    286
```

(2) INFORMATION FOR SEQ ID NO: 14:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..105

(xi) SEQUENCE DESCRIPTION: SEQ ID NO: 14:

```
GAT CTG TGT AAG AAG TGT GAT CCA ACA GAG GTA GAG CTG GAC AAT CAG          48
```

```
Asp Leu Cys Lys Lys Cys Asp Pro Thr Glu Val Glu Leu Asp Asn Gln
 95                 100                 105                 110

ATA GTC ACT GCG ACT CAA AGC AAC ATT TGC GAT GAG GAC AGC GCT ACA            96
Ile Val Thr Ala Thr Gln Ser Asn Ile Cys Asp Glu Asp Ser Ala Thr
                115                 120                 125

CTT TGG ACG                                                                105
Leu Trp Thr
```

(2) INFORMATION FOR SEQ ID NO: 15:

(i) SEQUENCE CHARACTERISTICS:
    (A) LENGTH: 61 base pairs
    (B) TYPE: nucleic acid
    (C) STRANDEDNESS: single
    (D) TOPOLOGY: linear (xi) SEQUENCE DESCRIPTION: SEQ ID NO: 15:

```
GATCAGGAAG ATGAACGTAT TGTTCTGGTT GACAACAAGT GCAAGTGTGC TCGTATTACT       60
T                                                                        61
```

(2) INFORMATION FOR SEQ ID NO: 16:

(i) SEQUENCE CHARACTERISTICS:
    (A) LENGTH: 198 base pairs
    (B) TYPE: nucleic acid
    (C) STRANDEDNESS: single
    (D) TOPOLOGY: linear (xi) SEQUENCE DESCRIPTION: SEQ ID NO: 16:

```
GCGATGACGA CGATAAGGCC CAAACGGAGA CCTGTACTGT TGCGCCTCGT GAACGGCAAA        60

ACTGCGGATT CCCGGAAGTA ACACCCTCTC AGTGCGCTAA TAAAGGCTGC TGTTTTGATG       120

ACACGGTACG GGGCGTTCCG TGGTGCTTCT ACCCCAATAC AATTGACGTT CCGCCTGAAG       180

AAGAGTGCGA GCCGTAAG                                                    198
```

(2) INFORMATION FOR SEQ ID NO: 17:

(i) SEQUENCE CHARACTERISTICS:
    (A) LENGTH: 138 amino acids
    (B) TYPE: amino acid
    (D) TOPOLOGY: linear (ii) MOLECULE TYPE: protein (xi) SEQUENCE DESCRIPTION: SEQ ID NO: 17:

```
Asp Gln Glu Asp Glu Arg Ile Val Leu Val Asp Asn Lys Cys Lys Cys
  1               5                  10                  15

Ala Arg Ile Thr Ser Arg Ile Ile Arg Ser Ser Glu Asp Pro Asn Glu
                 20                  25                  30

Asp Ile Val Glu Arg Asn Ile Arg Ile Ile Val Pro Leu Asn Asn Arg
             35                  40                  45

Glu Asn Ile Ser Asp Pro Thr Ser Pro Leu Arg Thr Arg Phe Val Tyr
 50                  55                  60

His Leu Ser Asp Leu Cys Lys Lys Cys Asp Pro Thr Glu Val Glu Leu
 65                  70                  75                  80

Asp Asn Gln Ile Val Thr Ala Thr Gln Ser Asn Ile Cys Asp Glu Asp
                 85                  90                  95

Ser Ala Thr Glu Thr Cys Ser Thr Tyr Asp Arg Asn Lys Cys Tyr Thr
                100                 105                 110

Ala Val Val Pro Leu Val Tyr Gly Gly Glu Thr Lys Met Val Glu Thr
            115                 120                 125
```

Ala Leu Thr Pro Asp Ala Cys Tyr Pro Asp
    130                 135

(2) INFORMATION FOR SEQ ID NO: 18:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 18:

Asp Gln Lys Cys Lys Cys Ala Arg Ile Thr Ser Arg Ile Ile Arg Ser
1               5                   10                  15

Ser Glu Asp Pro Asn Glu Asp Ile Val Glu Arg Asn Ile Arg Ile Ile
            20                  25                  30

Val Pro Leu Asn Asn Arg Glu Asn Ile Ser Asp Pro Thr Ser Pro Leu
            35                  40                  45

Arg Thr Arg Phe Val Tyr His Leu Ser Asp Leu Cys Lys Lys Asp Glu
        50                  55                  60

Asp Ser Ala Thr Glu Thr Cys
65                  70

(2) INFORMATION FOR SEQ ID NO: 19:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO: 19:

Ser Arg Ile Ile Arg Ser Ser Glu Asp Pro Asn Glu Asp Ile Val Glu
1               5                   10                  15

Arg Asn Ile Arg Ile Ile Val Pro Leu Asn Asn Arg Glu Asn Ile Ser
            20                  25                  30

Asp Pro Thr Ser Pro Leu Arg Thr Arg Phe Val Tyr His Leu Ser Asp
        35                  40                  45

Leu (2) INFORMATION FOR SEQ ID NO: 20:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 20:

Asp Gln Lys Cys Lys Cys Ala Arg Ile Thr Ser Arg
1               5                   10

(2) INFORMATION FOR SEQ ID NO: 21:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 21:

```
Asp Leu Cys Lys Lys Asp Glu Asp Ser Ala Thr Glu Thr Cys
 1               5                  10
```

(2) INFORMATION FOR SEQ ID NO: 22:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO: 22:

```
Ser Thr Tyr Asp Arg Asn Lys Cys Tyr Thr Ala Val Val Pro Leu Val
 1               5                  10                  15

Tyr Gly Gly Glu Thr Lys Met Val Glu Thr Ala Leu Thr Pro Asp Ala
             20                  25                  30

Cys Tyr Pro Asp
         35
```

(2) INFORMATION FOR SEQ ID NO: 23:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO: 23:

```
Asp Asn Lys Cys Lys Cys Ala Arg Ile Thr Ser Arg Ile Ile Arg Ser
 1               5                  10                  15

Ser Glu Asp Pro Asn Glu Asp Ile Val Glu Arg Asn Ile Arg Ile Ile
             20                  25                  30

Val Pro Leu Asn Asn Arg Glu Asn Ile Ser Asp Pro Thr Ser Pro Leu
             35                  40                  45

Arg Thr Arg Phe Val Tyr His Leu Ser Asp Leu Cys Lys Lys Cys Asp
         50                  55                  60

Pro Thr Glu Val Glu Leu Asp Asn Gln Ile Val Thr Ala Thr Gln Ser
 65                  70                  75                  80

Asn Ile Cys Asp Glu Asp Ser Ala Thr Glu Thr Cys Tyr
                 85                  90
```

(2) INFORMATION FOR SEQ ID NO: 24:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO: 24:

```
Asp Leu Cys Lys Lys Cys Asp Pro Thr Glu Val Glu Leu Asp Asn Gln
 1               5                  10                  15

Ile Val Thr Ala Thr Gln Ser Asn Ile Cys Asp Glu Asp Ser Ala Thr
             20                  25                  30

Leu Trp Thr
         35
```

(2) INFORMATION FOR SEQ ID NO: 25:

(i) SEQUENCE CHARACTERISTICS:
        (A) LENGTH: 22 amino acids (B) TYPE: amino acid
        (C) STRANDEDNESS:
        (D) TOPOLOGY: linear (xi) SEQUENCE DESCRIPTION: SEQ ID NO: 25:

Asp Gln Glu Asp Glu Arg Ile Val Leu Val Asp Asn Lys Cys Lys Cys
1               5                  10                  15

Ala Arg Ile Thr Ser Arg
            20

(2) INFORMATION FOR SEQ ID NO: 26:

(i) SEQUENCE CHARACTERISTICS:
        (A) LENGTH: 66 amino acids
        (B) TYPE: amino acid
        (C) STRANDEDNESS:
        (D) TOPOLOGY: linear (xi) SEQUENCE DESCRIPTION: SEQ ID NO: 26:

Cys Ser Asp Asp Asp Lys Ala Gln Thr Glu Thr Cys Thr Val Ala
1               5                  10                  15

Pro Arg Glu Arg Gln Asn Cys Gly Phe Pro Gly Val Thr Pro Ser Gln
            20                  25                  30

Cys Ala Asn Lys Gly Cys Cys Phe Asp Asp Thr Val Arg Gly Val Pro
                35                  40                  45

Trp Cys Phe Tyr Pro Asn Thr Ile Asp Val Pro Pro Glu Glu Glu Cys
    50                  55                  60

Glu Phe
65

(2) INFORMATION FOR SEQ ID NO: 27:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (xi) SEQUENCE DESCRIPTION: SEQ ID NO: 27:

CTAGTCCTTC TACTTGCATA ACAAGACCAA CTGTTGTTCA CGTTCACACG AGCATAATGA      60

AGATCTTAGT AGGCATCGAG TCTCCTGGGT TTACTTCTAT ATCAGCTTGC ATTGTAGGCA     120

TAGTAGCAGG GTGACTTATT GGCCCTCTTA TAGAGTCTAG GATGTTCAGG CAACGCGTGT     180

GCGAAGCATA TGGTGGACAG TCTAGACACA TTCTTCACAC TAGGTTGTCT CCATCTCGAC     240

CTGTTAGTCT ATCAGTGACG CTGAGTTTCG TTGTAAACGC TACTCCTGTC GCGATGTCTT     300

TGGACGTCGT GGATGCTATC CTTGTTTACG ATGTGCCGGC ACCAAGGCGA GCACATACCA     360

CCTCTCTGTT TTTACCACCT TTGACGGGAA TGCGGGCTAC GTACGATAGG CCTGACTTAA     420

G                                                                    421

(2) INFORMATION FOR SEQ ID NO: 28:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO: 28:

CTAGTCTTCA CGTTCACACG AGCATAATGA AGATCTTAGT AGGCATCGAG TCTCCTGGGT      60

TTACTTCTAT ATCAGCTTGC ATTGTAGGCA TAGTAGCAGG GTGACTTATT GGCCCTCTTA     120

TAGAGTCTAG GATGTTCAGG CAACGCGTGT GCGAAGCATA TGGTGGACAG TCTAGACACA        180

TTCTTCCTAC TCCTGTCGCG ATGTCTTTGG ACGACTTAA                              219

(2) INFORMATION FOR SEQ ID NO: 29:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO: 29:

TTAGTAGGCA TCGAGTCTCC TGGGTTTACT TCTATATCAG CTTGCATTGT AGGCATAGTA        60

GCAGGGTGAC TTATTGGCCC TCTTATAGAG TCTAGGATGT TCAGGCAACG CGTGTGCGAA       120

GCATATGGTG GACAGTCTAG                                                   140

(2) INFORMATION FOR SEQ ID NO: 30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 30:

TCTTCACGTT CACACGAGCA TAATGAAGAT C                                       31

(2) INFORMATION FOR SEQ ID NO: 31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO: 31:

ACACATTCTT CCTACTTCTC AGGCGATGTC TTTGGACGAC TTAA                          44

(2) INFORMATION FOR SEQ ID NO: 32:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (xi) SEQUENCE DESCRIPTION: SEQ ID NO: 32:

ACGTCGTGGA TGCTATCCTT GTTTACGATG TGCCGGCACC AAGGCGAGCA CATACCACCT         60

CTCTGTTTTT ACCACCTTTG ACGGGAATGC GGGCTACGTA CGATGGGACT GACTTAA           117

(2) INFORMATION FOR SEQ ID NO: 33:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO: 33:

CTGTTGTTCA CGTTCACACG AGCATAATGA AGATCTTAGT AGGCATCGAG TCTCCTGGGT         60

TTACTTCTAT ATCAGCTTGC ATTGTAGGCA TAGTAGCAGG GTGACTTATT GGCCCTCTTA       120

TAGAGTCTAG GATGTTCAGG CAACGCGTGT GCGAAGCATA TGGTGGACAG TCTAGACACA       180

```
TTCTTCACAC TAGGTTGTCT CCATCTCGAC CTGTTAGTCT ATCAGTGACG CTGAGTTTCG    240

TTGTAAACGC TACTCCTGTC GCGATGTCTT TGGACGATGA CT                       282
```

(2) INFORMATION FOR SEQ ID NO: 34:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO: 34:

```
GATCTGTGTA AGAAGTGTGA TCCAACAGAG GTAGAGCTGG ACAATCAGAT AGTCACTGCG    60

ACTCAAAGCA ACATTTGCGA TGAGGACAGC GCTACACTTT GGACG                    105
```

(2) INFORMATION FOR SEQ ID NO: 35:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO: 35:

```
CTAGTCCTTC TACTTGCATA ACAAGACCAA CTGTTGTTCA CGTTCACACG AGCATAATGA    60

AGATC                                                                65
```

(2) INFORMATION FOR SEQ ID NO: 36:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (xi) SEQUENCE DESCRIPTION: SEQ ID NO: 36:

```
ACTTCGCTAC TGCTGCTATT CCGGGTTTGC CTCTGGACAT GACAACGCGG AGCACTTGCC    60

GTTTTGACGC CTAAGGGCCT TCATTGTGGG AGAGTCACGC GATTATTTCC GACGACAAAA   120

CTACTGTGCC ATGCCCCGCA AGGCACCACG AAGATGGGGT TATGTTAACT GCAAGGCGGA   180

CTTCTTCTCA CGCTCGGCAT TCTTAA                                        206
```

(2) INFORMATION FOR SEQ ID NO: 37:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO: 37:

```
Asp Gln Glu Asp Glu Arg Ile Val Leu Val Asp Asn Lys
1               5                   10
```

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO: 38:

```
Glu Asn Leu Tyr Phe Gln Ser
1               5
```

(2) INFORMATION FOR SEQ ID NO: 39:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO: 39:

```
Lys Ala His Lys Val Asp Met Val Gln Tyr Thr
1               5                       10
```

(2) INFORMATION FOR SEQ ID NO: 40:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO: 40:

```
Val Gln Tyr Thr
1
```

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO: 41:

```
Glu Lys Ala Val Ala Asp
1               5
```

(2) INFORMATION FOR SEQ ID NO: 42:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..78

(xi) SEQUENCE DESCRIPTION: SEQ ID NO: 42:

```
ATG AAA TTC TTA GTC AAC GTT GCC CTT TTT ATG GTC GTA TAC ATT TCT         48
Met Lys Phe Leu Val Asn Val Ala Leu Phe Met Val Val Tyr Ile Ser
            40                  45                  50

TAC ATC TAT GCG GAT CCG AGC TCG AGT GCT CTAGATCTGC AGCTGGTACC           98
Tyr Ile Tyr Ala Asp Pro Ser Ser Ser Ala
            55                  60

ATGGAATTCG AAGCTTGGAG TCGACTCTGC TGA                                   131
```

(2) INFORMATION FOR SEQ ID NO: 43:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 43:

Met Lys Phe Leu Val Asn Val Ala Leu Phe Met Val Val Tyr Ile Ser
 1               5                  10                  15

Tyr Ile Tyr Ala Asp Pro Ser Ser Ser Ala
                20                  25

(2) INFORMATION FOR SEQ ID NO: 44:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO: 44:

Lys Asp Glu Leu
 1

(2) INFORMATION FOR SEQ ID NO: 45:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO: 45:

Ala Ile Gln Asp Pro Arg Leu Phe Ala Glu Glu Lys Ala Val Ala Asp
 1               5                  10                  15

(2) INFORMATION FOR SEQ ID NO: 46:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 46:

GATCAGGAAG ATGAACGTAT TGTTCTGGTT GACAACAAGT GCAAGTGTGC TCGTATTACT         60

T                                                                        61

(2) INFORMATION FOR SEQ ID NO: 47:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 47:

CTAGAAGTAA TACGAGCACA CTTGCACTTG TTGTCAACCA GAACAATACG TTCATCTTCC         60

T                                                                        61

(2) INFORMATION FOR SEQ ID NO: 48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 48:

GATCAGAAGT GCAAGTGTGC TCGTATTACT T                                       31

(2) INFORMATION FOR SEQ ID NO: 49:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 49:

```
CTAGAAGTAA TACGAGCACA CTTGCACTTC T                              31
```

(2) INFORMATION FOR SEQ ID NO: 50:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 50:

```
GATCAGGAAG ATGAACGTAT TGTTCTGGTT GACAACAAGT GCAAGTCCGC TCGTATTACT    60
T                                                                   61
```

(2) INFORMATION FOR SEQ ID NO: 51:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 51:

```
CTAGAAGTAA TACGAGCGGA CTTGCACTTG TTGTCAACCA GAACAATACG TTCATCTTCC    60
T                                                                   61
```

(2) INFORMATION FOR SEQ ID NO: 52:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 52:

```
GATCAGGAAG ATGAACGTAT TGTTCTGGTT GACAACAAGT GCAAGGTTGC TCGTATTACT    60
T                                                                   61
```

(2) INFORMATION FOR SEQ ID NO: 53:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO: 53:

```
CTAGAAGTAA TACGAGCAAC CTTGCACTTG TTGTCAACCA GAACAATACG TTCATCTTCC    60
T                                                                   61
```

(2) INFORMATION FOR SEQ ID NO: 54:

(i) SEQUENCE CHARACTERISTICS:
        (A) LENGTH: 47 base pairs (B) TYPE: nucleic acid
        (C) STRANDEDNESS: single
        (D) TOPOLOGY: linear (xi) SEQUENCE DESCRIPTION: SEQ ID NO: 54:

CTAGAATCAT CCGTAGCTCA GAGGACCCAA ATGAAGATAT AGTCGAA                47

(2) INFORMATION FOR SEQ ID NO: 55:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO: 55:

GATACGGATG TTACGTTCGA CTATATCTTC ATTTGGGTCC TCTGAGCTAC GGATGATT    58

(2) INFORMATION FOR SEQ ID NO: 56:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 56:

CGTAACATCC GTATCATCGT CCCACTGAAT AACCGGGAGA ATATCTCAG              49

(2) INFORMATION FOR SEQ ID NO: 57:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 57:

CGTAACATCC GTATCATCGT CCCACTGAAT AACCGGGAGC ACATCTCAG              49

(2) INFORMATION FOR SEQ ID NO: 58:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 58:

ACGGACTTGT AGGATCTGAG ATATTCTCCC GGTTATTCAG TGGGACGAT              49

(2) INFORMATION FOR SEQ ID NO: 59:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 59:

ACGGACTTGT AGGATCTGAG ATGTGCTCCC GGTTATTCAG TGGGACGAT              49

(2) INFORMATION FOR SEQ ID NO: 60:

(i) SEQUENCE CHARACTERISTICS:
        (A) LENGTH: 44 base pairs
        (B) TYPE: nucleic acid (C) STRANDEDNESS: single
                (D) TOPOLOGY: linear (xi) SEQUENCE DESCRIPTION: SEQ ID NO: 60:

ATCCTACAAG TCCGTTGCGC ACACGCTTCG TATACCACCT GTCA                         44

(2) INFORMATION FOR SEQ ID NO: 61:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (xi) SEQUENCE DESCRIPTION: SEQ ID NO: 61:

GATCTGACAG GTGGTATACG AAGCGTGTGC GCA                                    33

(2) INFORMATION FOR SEQ ID NO: 62:

(i) SEQUENCE CHARACTERISTICS:
                (A) LENGTH: 60 base pairs
                (B) TYPE: nucleic acid
                (C) STRANDEDNESS: single
                (D) TOPOLOGY: linear (xi) SEQUENCE DESCRIPTION: SEQ ID NO: 62:

GATCTGTGTA AGAAGTGTGA TCCAACAGAG GTAGAGCTGG ACAATCAGAT AGTCACTGCA       60

(2) INFORMATION FOR SEQ ID NO: 63:

(i) SEQUENCE CHARACTERISTICS:
                (A) LENGTH: 44 base pairs
                (B) TYPE: nucleic acid
                (C) STRANDEDNESS: single
                (D) TOPOLOGY: linear (xi) SEQUENCE DESCRIPTION: SEQ ID NO: 63:

GATCTGTGTA AGAAGGATGA GGACAGCGCT ACAGAAACCT GCTG                        44

(2) INFORMATION FOR SEQ ID NO: 64:

(i) SEQUENCE CHARACTERISTICS:
                (A) LENGTH: 44 base pairs
                (B) TYPE: nucleic acid
                (C) STRANDEDNESS: single
                (D) TOPOLOGY: linear (xi) SEQUENCE DESCRIPTION: SEQ ID NO: 64:

AATTCAGCAG GTTTCTGTAG CGCTGTCCTC ATCCTTCTTA CACA                        44

(2) INFORMATION FOR SEQ ID NO: 65:

(i) SEQUENCE CHARACTERISTICS:
                (A) LENGTH: 62 base pairs
                (B) TYPE: nucleic acid
                (C) STRANDEDNESS: single
                (D) TOPOLOGY: linear (xi) SEQUENCE DESCRIPTION: SEQ ID NO: 65:

GATCTGTGTA AGAAGGATGA GGACAGCGCT ACAGAAACCT GCTACGAGAA GGATGAGCTG       60
TG                                                                      62

(2) INFORMATION FOR SEQ ID NO: 66:

(i) SEQUENCE CHARACTERISTICS:
                (A) LENGTH: 62 base pairs (B) TYPE: nucleic acid
        (C) STRANDEDNESS: single
        (D) TOPOLOGY: linear (xi) SEQUENCE DESCRIPTION: SEQ ID NO: 66:

AATTCACAGC TCATCCTTCG CGTCGCAGGT TTCTGTAGCG CTGTCCTCAT CCTTCTTACA    60

CA    62

(2) INFORMATION FOR SEQ ID NO: 67:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO: 67:

GATCTGTGTA AGAAGTCTGA TATCGATGAA GATTCCGCTA CAGAAACCTG CAGCACATG    59

(2) INFORMATION FOR SEQ ID NO: 68:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO: 68:

AATTCATGTG CTGCAGGTTT CTGTAGCGGA ATCTTCATCG ATATCAGACT TCTTACACA    59

(2) INFORMATION FOR SEQ ID NO: 69:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO: 69:

GATCTGTCTA AGAAGTCTGA TATCGATGAA GATTACAGAT TCTTCAGACT ATAGCTACTT    60

CTAA    64

(2) INFORMATION FOR SEQ ID NO: 70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 70:

AATCTTCATC GATATCAGAC TTCTTAGACA    30

(2) INFORMATION FOR SEQ ID NO: 71:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO: 71:

GATCTGGTTA AGAAGTCTGA TATCGATGAA GATTACCAAT TCTTCAGACT ATAGCTACTT    60

CTAA    64

(2) INFORMATION FOR SEQ ID NO: 72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 72:

```
AATCTTCATC GATATCAGAC TTCTTAACCA                                30
```

(2) INFORMATION FOR SEQ ID NO: 73:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 73:

```
ATTGTCCAGC TCTACCTCTG TTGGATCACA CTTCTTACAC A                   41
```

(2) INFORMATION FOR SEQ ID NO: 74:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 74:

```
ACTCAAAGCA ACATTTGCGA TGAGGACAGC GCTACAGAAA CCTGCA              46
```

(2) INFORMATION FOR SEQ ID NO: 75:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 75:

```
GGTTTCTGTA GCGCTCTGCT CATCGCAAAT GTTGCTTTGA GTCGCAGTGA CTATCTG  57
```

(2) INFORMATION FOR SEQ ID NO: 76:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO: 76:

```
GCACCTACGA TAGGAACAAA TGCTACACGG CCGTGGTTCC GCTCGTGTAT GGTGGAGAG  59
```

(2) INFORMATION FOR SEQ ID NO: 77:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 77:

```
GAGCGGAACC ACGGCCGTGT AGCATTTGTT CCTATCGTAG GTGCTGCA            48
```

(2) INFORMATION FOR SEQ ID NO: 78:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 78:

```
ACAAAAATGG TGGAAACTGC CCTTACGCCC GATGCATGCT ATCCGGACTG            50
```

(2) INFORMATION FOR SEQ ID NO: 79:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO: 79:

```
AATTCAGTCC GGATAGCATG CATCGGGCGT AAGGGCAGTT TCCACCATTT TTGTCTCTCC    60

ACCATACAC                                                           69
```

(2) INFORMATION FOR SEQ ID NO: 80:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO: 80:

```
ACAAAAATGG TGGAAACTGC CCTTACGCCC GATGCATGCT ATCCGGACAA GGATGAATTG    60

TG                                                                  62
```

(2) INFORMATION FOR SEQ ID NO: 81:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 81:

```
AATTCACAAT TCATCCTTGT CCGGATAGCA TGCATCGGGC GTAAGGGCAG TTTCCACCAT    60

TTTTGTCTCT CCACCATACA C                                             81
```

(2) INFORMATION FOR SEQ ID NO: 82:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 82:

```
GATCAGGTCG CTGCCATCCA AGACCCGAGG CTGTTCGCCG AAGAGAAGGC CGTCGCTGAC    60

TCCAAGTGCA AGTGTGCTCG TATTACTT                                      88
```

(2) INFORMATION FOR SEQ ID NO: 83:

(i) SEQUENCE CHARACTERISTICS:
        (A) LENGTH: 88 base pairs
        (B) TYPE: nucleic acid
        (C) STRANDEDNESS: single (D) TOPOLOGY: linear (xi) SEQUENCE DESCRIPTION: SEQ ID NO: 83:

CTAGAAGTAA TACGAGCACA CTTGCACTTG GAGTCAGCGA CGGCCTTCTC TTCGGCGAAC      60

AGCCTCGGGT CTTGGATGGC AGCGACCT                                        88

(2) INFORMATION FOR SEQ ID NO: 84:

(i) SEQUENCE CHARACTERISTICS:
         (A) LENGTH: 77 base pairs
         (B) TYPE: nucleic acid
         (C) STRANDEDNESS: single
         (D) TOPOLOGY: linear (xi) SEQUENCE DESCRIPTION: SEQ ID NO: 84:

GCGATGACGA CGATAAGGCC CAAACGGAGA CCTGTACTGT TGCGCCTCGT GAACGGCAAA      60

ACTGCGGATT CCCGGAA                                                    77

(2) INFORMATION FOR SEQ ID NO: 85:

(i) SEQUENCE CHARACTERISTICS:
         (A) LENGTH: 66 base pairs
         (B) TYPE: nucleic acid
         (C) STRANDEDNESS: single
         (D) TOPOLOGY: linear (xi) SEQUENCE DESCRIPTION: SEQ ID NO: 85:

GTTTTGCCGT TCACGAGGCG CAACAGTACA GGTCTCCGTT TGGGCCTTAT CGTCGTCATC      60

GCTTCA                                                                66

(2) INFORMATION FOR SEQ ID NO: 86:

(i) SEQUENCE CHARACTERISTICS:
         (A) LENGTH: 72 base pairs
         (B) TYPE: nucleic acid
         (C) STRANDEDNESS: single
         (D) TOPOLOGY: linear (xi) SEQUENCE DESCRIPTION: SEQ ID NO: 86:

GTAACACCCT CTCAGTGCGC TAATAAAGGC TGCTGTTTTG ATGACACGGT ACGGGGCGTT      60

CCGTGGTGCT TC                                                         72

(2) INFORMATION FOR SEQ ID NO: 87:

(i) SEQUENCE CHARACTERISTICS:
         (A) LENGTH: 72 base pairs
         (B) TYPE: nucleic acid
         (C) STRANDEDNESS: single
         (D) TOPOLOGY: linear (xi) SEQUENCE DESCRIPTION: SEQ ID NO: 87:

GCCCCGTACC GTGTCATCAA AACAGCAGCC TTTATTAGCG CACTGAGAGG GTGTTACTTC      60

CGGGAATCCG CA                                                         72

(2) INFORMATION FOR SEQ ID NO: 88:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (xi) SEQUENCE DESCRIPTION: SEQ ID NO: 88:

```
                                   -continued

TACCCCAATA CAATTGACGT TCCGCCTGAA GAAGAGTGCG AGCCGTAAG              49

(2) INFORMATION FOR SEQ ID NO: 89:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO: 89:

AATTCTTACG GCTCGCACTC TTCTTCAGGC GGCAAGTCAA TTGTATTGGG GTAGAAGCAC   60

CACGGAAC                                                           68
```

EPITHELIAL CELL TARGETING AGENT

TECHNICAL FIELD

The present invention relates generally to the targeting of therapeutic compounds to specific cells. The invention is more particularly related to targeting molecules for use in delivering compounds to non-polarized epithelial cells. Such targeting molecules may be used in a variety of therapeutic procedures.

BACKGROUND OF THE INVENTION

Improving the delivery of drugs and other agents to target tissues has been the focus of considerable research for many years. Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the epithelial barrier, resulting in undesirable systemic distribution, or (b) temporary residence of the drug within the gastrointestinal tract. Accordingly, a major goal has been to develop methods for specifically targeting agents to cells and tissues that may benefit from the treatment, and to avoid the general physiological effects of inappropriate delivery of such agents to other cells and tissues.

In addressing this issue, some investigators have attempted to use chimeric molecules that bind to growth factor receptors on gastrointestinal epithelial cells to facilitate transepithelial transport of therapeutic agents (see WO 93/20834). However, these methods have several disadvantages. For example, such chimeric molecules are transcytosed through the epithelium from the gut lumen and absorbed into the blood stream, resulting in systemic distribution and removal from the epithelium proper. Since the therapeutic agents are targeted specifically away from the epithelium for systemic distribution, these chimeric molecules are generally not useful for treatment of epithelium associated conditions. In addition, TGF-γ or other molecules binding to EGF receptors exhibit many or all of the apparent biological activities of EGF, such as stimulation of enterocyte mitogenesis or suppression of gastric secretion. Such effects collateral to the transcytotic uptake of therapeutic agents may not be desirable or may be contraindicated for intervention of epithelium associated conditions or diseases. Furthermore, EGF receptors are not unique to epithelial cells of the gastrointestinal tract, and can be found on numerous other cells including kidney cells and hepatocytes. Thus, molecules which have affinity for the EGF receptor and are distributed systemically in the blood can be rapidly removed from circulation, accumulated in specific organs and potentially degraded or secreted.

Within an alternative approach, other investigators have employed Fab fragments of an anti-polymeric immunoglobulin receptor IgG to target DNA to epithelial cells in vitro that contain such a receptor (see Ferkol et al., *J. Clin. Invest.* 92:2394–2400, 1993). Still other researchers have described the translocation of a chimeric IgA construct across a monolayer of epithelial cells in vitro (see Terskikh et al., *Mol. Immunol.* 31:1313–1319, 1994). Others have used ascites tumor implants in vivo in mice and observed an IgA dimeric antibody produced by subcutaneous tumor cells to accumulate in feces, suggesting that IgA is transported across an epithelial barrier of the gastrointestinal tract (see Greenberg et al., *Science* 272: 104–107, 1996).

Although epithelial cells are normally aligned with one another to form a protective barrier, preventing bodily entry of toxins and pathogens, aberrations in this cellular alignment are often indicative of disease. In particular, non-polarized epithelial cells present in blood or lymphatic fluid are often indicative of metastatic disease. Eradication of metastatic cells is a fundamental goal of cancer therapy, but conventional techniques such as chemotherapy often result in undesirable side effects.

There remains a need in the art for systems for delivering agents to target epithelial cells, particularly non-polarized epithelial cells which are not aligned with another epithelial cell or cells. The present invention fulfills these needs and further provides other related advantages.

SUMMARY OF THE INVENTION

Briefly stated, the present invention provides targeting molecules for the specific delivery of biological agents to epithelial cells. Within certain aspects, the present invention provides a targeting molecule linked to at least one biological agent, wherein the targeting molecule comprises a polypeptide that (a) forms a closed covalent loop; and (b) contains at least three peptide domains having β-sheet character, each of the domains being separated by domains lacking β-sheet character, such that the biological agent is capable of entering and killing a non-polarized epithelial cell. Within specific embodiments, the targeting molecule is linked to at least one biological agent by a substrate for an intracellular or extracellular enzyme associated with or secreted from a non-polarized epithelial cell.

Within another aspect, the present invention provides a pharmaceutical composition comprising a targeting molecule linked to at least one biological agent, as described above, in combination with a pharmaceutically acceptable carrier.

In further aspects, methods are provided for treating a patient afflicted with a disease associated with non-polarized epithelial cells, comprising administering to a patient a pharmaceutical composition as described above. Such diseases include non-small cell lung carcinoma, breast carcinoma, colon carcinoma, ovarian carcinoma, prostate carcinoma, and endometriosis.

Within related aspects, the present invention provides methods for inhibiting the development in a patient of a disease associated with non-polarized epithelial cells, comprising administering to a patient a pharmaceutical composition as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWING

FIG. 1 is a comparison of native J chain sequences reported for human (top line) (SEQ ID NO:1), mouse (second line) (SEQ ID NO:2), rabbit (third line) (SEQ ID NO:3), cow (fourth line) (SEQ ID NO:4), bull frog (fifth line) (SEQ ID NO:5) and earth worm (sixth line) (SEQ ID NO:6). For each non-human sequence, amino acid residues that are identical to those in the human sequence are indicated by a dash. Residues that differ from the human sequence are indicated using standard one letter abbreviations.

DETAILED DESCRIPTION OF THE INVENTION

As noted above, the present invention is generally directed to targeting molecules (TMs) for use in the delivery of biological agents to non-polarized epithelial cells. Upon delivery to an epithelial cell, the agent may remain within the cell or may undergo transepithelial transport via transcytosis. For example, the agent and TM may be transported through the plasma membrane and remain within the epithelial cell, or the agent may remain within the cell while the TM undergoes transepithelial transport. Agents that remain within the epithelial cell may modify an activity or function of a cellular component or a foreign component, such as a virus.

Prior to setting forth the present invention in detail, definitions of certain terms used herein are provided.

Epithelial surface (or epithelial barrier): A surface lining the exterior of the body, an internal closed cavity of the body or body tubes that communicate with the exterior environment. Epithelial surfaces generally comprise aligned epithelial cells, and include the genitourinary, respiratory, alimentary, ocular conjunctiva, nasal, oral and pharyngeal cavities, as well as the ducts and secretory portions of glands and receptors of sensory organs. The term "epithelial surface" as used herein is synonymous with "epithelial barrier." One side of an epithelial surface is free of adherence to cellular and extracellular components, other than coating substances and secretions. The other side of the surface is normally adjacent to the basement membrane and is exposed to interstitial fluids and components of the underlying tissues. Epithelial surfaces are typically formed from cells in close apposition to one another, the contact between plasma membranes of adjacent cells characterized by a tight junction (zonula occludens) which delimits the outside and inside domains of an epithelial surface. An experimental epithelial-like surface can be generated in vitro with autonomously replicating cell lines (e.g., MDCK, ATCC No. CCL34; HEC-1A, ATCC No. HTB 112), which form epithelial-like surfaces in culture, have tight junctions and articulate one free (apical) and one adherent (basolateral) domain.

Non-polarized epithelial (NPE) cells: Cells that arise from epithelial surfaces but that are not present within an epithelial surface having a basolateral domain, apical domain or zonula occludens. An epithelial surface can create and release NPE cells by a variety of processes including tumorigenesis, tumor metastases, and inflammatory hyperplasia. NPE cells can exist free in bodily fluids or can be joined with other individual epithelial cells in an abnormal association containing no zonula occludens, basolateral domain or apical domain. NPE cells are associated with neoplastic epithelial growth, ulcerative colitis and epithelial inflammations causing hyperplastic cell growth. NPE cells may be identified by immunohistochemical staining techniques utilizing either anti-secretory component, anti-IgA, or anti-IgM as described, for example, by Brandtzaeg, *Scand. J. Immunol.* 22:111–146, 1985. NPE cells may also be identified by immunohistochemical techniques utilizing anti-secretory component or monoclonal antibody Ber-EP4 (see Latza et al., *J. Clin. Path.* 43:213–220, 1990.)

Apical domain: The outside of an epithelial surface which is adjacent to the environment external to the body or to the volume of a body cavity or body tube. The outside of the cells, as delimited by the zonula occludens, is composed of the coating substances, secretions and cell membranes facing the outside of the epithelial surface.

Luminal compartment: The inner space of a body tube, cavity or duct lined by an epithelial surface and adjacent to the apical domain.

Basolateral domain: The inside of the epithelial surface which is delimited from the apical domain by the zonula occludens. The basolateral domain is adjacent to the basement membrane and is exposed to interstitial fluids and components of the tissues underlying epithelial surfaces. The basolateral domain is the inner side of cells of an epidermal surface.

Basolateral membrane: The portion of the plasma membrane of a cell of an epithelial surface which is within the basolateral domain.

Basolateral factor: A component of the basolateral domain which is a naturally occurring element of a basolateral membrane in vivo. A "basolateral factor associated with an epithelial surface" refers to a basolateral factor attached by covalent or noncovalent bonds to a basolateral domain, or a component of the membrane proper in a basolateral domain.

Internalization: The process of uptake into a cell compartment that is bounded by a plasma membrane.

Specific binding: A TM specifically binds to an NPE cell if it specifically interacts with a receptor on the plasma membrane of the NPE cell. A TM specifically binds to a basolateral domain if it specifically interacts at the basolateral domain of an epithelial surface. Both quantitative and qualitative assays may be used to distinguish specific binding from binding which is not specific within the context of the subject invention. A quantitative measurement of binding affinity ($k_{aff}$) may be used to identify components that bind specifically. In general, a $k_{aff}$ of $10^4$ $M^{-1}$ or higher constitutes specific binding between two binding components. The binding affinity for the cognate components of a binding interaction can be estimated experimentally by a variety of methods that are well known in the art, including equilibrium dialysis assays, precipitation radioimmunoassays, assays with immobilized ligands, assays with isolated cells or membranes, ELISAs, or by other direct or indirect measurements or binding (e.g., plasmon resonance).

Qualitative specificity of binding may be demonstrated by differential, or asymmetric distribution of binding of a factor among two or more chemical, spatial or temporal domains. This differential distribution can be observed visually, or by chemical or physical means, and generally reflects approximately at least a 3 to 1 differential in signal intensity between NPE cell and non-epithelial plasma membranes. TMs are also capable of binding to factors on NPE cells which originate from epithelial surfaces. Such qualitative specificity may result from substantial differences in the affinity of binding of an agent to the number or availability of cognate binding sites on plasma membranes. The qualitative specificity of binding of an agent among several cell types can be observed in a competition experiment. In such an experiment a TM is allowed to distribute among cell types, and at equilibrium is observed to preferentially bind to NPE cells over another cell type.

Targeting Molecule (TM): A molecule capable of specifically binding to a cognate factor on an NPE cell plasma membrane.

Biological agent: Any molecule, group of molecules, virus, component of a virus, cell or cell component that is synthesized by a cell or ex vivo, can be derived from a cell and/or can be demonstrated to modify the properties of a cell, and which is capable of killing a cell, following TM-facilitated entry. Such agents may be referred to herein as lethal agents. Biological agents may also include therapeutic agents (i.e., drugs and other medicinal compounds useful for treating or preventing a disorder or regulating the physiology of a patient).

Linked: A biological agent is linked to a TM if it is attached covalently, by ionic interaction and/or by hydrophobic interactions, or by other means such that under physiological conditions of pH, ionic strength and osmotic potential the linked entities are associated with each other at equilibrium.

TMs as described herein are generally capable of specifically binding to a factor preferentially distributed on an epithelial surface, such as a basolateral factor. TMs are also capable of binding to such a factor in NPE cells that originate from epithelial surfaces. Through binding to such a factor, TMs are capable of causing the internalization of a biological agent linked to the TM. TMs as described herein have a distinct three-dimensional structure. In general, TMs comprise a polypeptide that forms a closed covalent loop which is referred to herein as the "core." All subunits of the polypeptide may, but need not, be connected by identical chemical bonds. In a preferred embodiment, the polypeptide comprises amino and/or imino acids covalently joined by peptide bonds and one or more cystine disulfide bridges.

The core of a TM typically contains at least three peptide domains having β-sheet character, interspersed among regions lacking β-sheet character. In this regard, a "peptide domain" is a portion of a polypeptide comprising at least three amino acid residues. A peptide domain is said to have β-sheet character if the peptide backbone has an extended conformation with side-chain groups in a near planar and alternating arrangement such that hydrogen bonding can occur between carbonyl and NH groups of the backbone of adjacent β-strands. Furthermore, TMs generally contain at least one cysteine residue not present within an intramolecular cystine. Such cysteine(s) may be used for linking one or more biological agents to the TM, although other means of linking biological agents are also contemplated.

One or more of a variety of other structures may, but need not, be additionally present within a TM. For example, a second peptide loop may be present within the core sequence. Additional N-terminal and/or C-terminal sequences may be present. If present, N-terminal sequences are usually linear. A preferred N-terminal sequence is a short (about 1–20 amino acid residues) peptide domain. C-terminal sequences may be linear and/or may form one or more loops. Such sequences may, but need not, possess domains having β-sheet character. These and/or other protein domains may be added to the core by genetic means or chemically, using covalent bonds or noncovalent interactions.

In a preferred embodiment, a TM comprises all or a portion of a native J chain sequence, or a variant thereof. J chain is a 15 kD protein that, in vivo, links IgM or IgA monomers to form pentameric IgM or dimeric IgA (see Max and Korsmeyer, *J. Exp. Med.* 161:832–849, 1985). To date, sequences of J chains from six organisms have been deduced (see FIG. 1 and SEQ ID NO:1–SEQ ID NO:6; Kulseth and Rogne, *DNA and Cell Biol.* 13:37–42, 1994; Matsuuchi et al., *Proc. Natl. Acad Sci. USA* 83:456–460, 1986; Max and Korsmeyer, *J. Exp. Med.* 161:832–849, 1985; Hughes et al., *Biochem J.* 271:641–647, 1990; Mikoryak et al., *J. Immunol.* 140:4279–4285, 1988; Takahashi et al., *Proc. Natl. Acad. Sci. USA* 93:1886–1891, 1996). A TM may comprise a native J chain from one of these organisms, or from any other organism.

Alternatively, a TM may comprise a portion or variant of a native J chain sequence. A variant is a polypeptide that differs from a native a sequence only in one or more substitutions and/or modifications. Portions and variants of the native J chain sequence contemplated by the present invention are those that substantially retain the ability of the native J chain to specifically bind to an NPE cell, and cause the internalization of a linked biological agent. Such portions and variants may be identified using, for example, the representative assays described herein.

Within the context of the TM compositions provided herein, the TM is not full length dimeric IgA. More specifically, the TM does not contain all of the components present within a naturally-occurring IgA (i.e., a heavy chain containing contiguous variable, $C_H1\alpha$, $C_H2\alpha$ and $C_H3\alpha$ domains and a light chain containing contiguous variable and $C_L$ domains). Such a TM may, of course, contain one or more portions of an IgA molecule, including an IgM.

As noted above, specific binding may be evaluated using quantitative and/or qualitative methods. In one representative quantitative assay, secretory component (SC) isolated from human milk by standard immunoaffinity chromatography methods (Underdown et al., *Immunochemistry* 14:111–120, 1977) is immobilized on a CM5 sensor chip with a BIACORE apparatus (Pharmacia, Piscataway, N.J.) by primary amine coupling. The sensor chip is activated by injection of 30 μL of 0.05M N-hydroxysuccinimide and N-ethyl-N-(3-diethylaminopropyl)carbodiimide, followed by injection of 25 μL of human SC (15 μg/mL) in 10 mM sodium acetate, pH 5.0. Unreacted carbodiimide is then quenched with 30 μL ethanolamine. All reagents are delivered at a flow rate of 5 μL per minute. To evaluate the kinetics of binding and desorption, serial two fold dilutions of TMs at concentrations between 100 μM and 100 nM are injected in binding buffer: 25 mM Tris, pH 7.2, 100 mM NaCl, 10 mM $MgCl_2$ at a flow rate of 20 μL per minute. Between dilutions, the surface is regenerated by injecting 50 μL of 25 mM Tris, pH 7.2, 200 mM NaCl, 2M urea, followed by injecting 50 μL of binding buffer. Association and dissociation constants are derived from sensograms using BIAevaluation 2.1 software to derive simple association($k_a$) and dissociation constants($k_d$). The $K_{aff}$ is estimated as $k_a/k_d$.

In one representative qualitative assay, monolayers of HEC-1 A cells can be used to measure qualitative binding of TMs. The procedure is based on previously published protocols (see Ball et al., *In Vitro Cell Biol.* 31: 96, 1995). HEC-1A cells are cultured on 24 mm filter transwells (Costar, #3412, 0.4 μm) for one week until cells are confluent. Monolayer-covered filter transwells are washed twice on both surfaces with cold PBS (4° C.). One ml of cold MEM-BSA containing 1.0 μg of biotinylated ligand is added to the apical chamber and 1.5 ml cold MEM-BSA buffer (MEM-BSA (4° C.): minimum essential medium with hank's salts, and 25 mM HEPES buffer without L-glutamine (Life Technologies, Gaithersburg, Md.; Cat. No. 12370) containing 0.5% BSA, which is treated at 56° C. for 30 min to inactivate endogenous protease and filter sterilized) containing 1.5 μg of biotinylated ligand is added to the basolateral chamber. The cultures are kept at 4° C. for 2 hours to achieve maximum binding in the absence of internalization. The medium is removed from both chambers, and the filters are washed twice with cold PBS. Filters are then remove from the transwell supports with a scalpel and incubated with a streptavidin-fluorescein conjugate (#21223, Pierce Chemical Company, Rockford, Ill.), 0.1 μg/mL in cold PBS, then washed 3 times with cold PBS. 1 cm square pieces of filter are then cut from the 24 mm filter and mounted on microscope slides and observed microscopically under epifluorescence illumination (excitation 490 nm, emission 520 nm). Under these conditions the apical membranes show little or no fluorescence, while basolateral membranes demonstrate bright fluorescence (i e., greater than a 3 to 1 differential in signal intensity) indicating specific binding to the basolateral domain. Similar assays can be employed with isolated epithelial tissues from gastrointestinal, oral or bronchial epithelial tissue layers.

Within another representative qualitative assay, individual HEC-1A cells can be used to measure qualitative binding of TMs. HEC-1A cells are cultured on 24 mm filter transwells (Costar, #3412, 0.4 μm) for one week until cells are confluent. Cells may then be disrupted by trypsinization and the individual disrupted cells collected by centrifugation. Cell pellets are washed twice with cold PBS. One ml of cold MEM-BSA containing 1.0 μg of biotinylated ligand is then added to the cells. The cells are kept at 4° C. for 2 hours to achieve maximum binding in the absence of internalization. The medium is removed from the cells, which are washed twice with cold PBS. Cells are then incubated with a streptavidin-fluorescein conjugate (#21223, Pierce Chemical Company, Rockford, Ill.), 0.1 μg/mL in cold PBS, then washed 3 times with cold PBS. Cells are then mounted on microscope slides and observed microscopically under epifluorescence illumination (excitation 490 nm, emission 520 nm). Under these conditions the plasma membranes of NPE cells show bright fluorescence (i.e., greater than a 3 to 1 differential in signal intensity compared to non-epithelial cella) indicating specific binding to the NPE cell surface. Similar assays can be employed with isolated epithelial tissues or NPE cells from gastrointestinal, oral or bronchial epithelial tissue layers.

Once bound to the plasma membrane of an NPE cell, a TM may be internalized within an NPE cell. Suitable cells for evaluating internalization include MDCK cells expressing the human polyimmunoglobulin receptor (pIgR) (see Tamer et al., J. Immunol. 155:707–714, 1995) and HEC1-A cells, as well as non-epithelial transgenic cells which express the polyimmunoglobulin gene. One assay in which internalization can be observed employs a HEC1-A cell line grown to confluent monolayers on permeable membrane supports (such as Costar, Cambridge, Mass., #3412). Briefly, 100 μg to 10 μg of a TM (e.g., fluorescein labeled) may be added to 1.5 mL of assay buffer in the basolateral compartment of cell monolayers and incubated at a temperature that allows binding and internalization of TMs, but that inhibits transcytosis (e.g., 90 minutes at 16° C.). The medium from both compartments is then removed and the filter membranes washed (e.g., twice at 4° C. with PBS). The membrane is immersed in a fixation solution of, for example, 3% (w/v) paraformaldehyde, 1% (w/v) glutaraldehyde, 5% (w/v) sucrose, 100 mM Na phosphate pH 7.4 on ice for 30 minutes. The membranes may be removed from the plastic insert by cutting around the periphery with a scalpel and cut into 5 mm square sections. These wholemount sections may be placed on microscope slides and observed microscopically under epifluorescence illumination (excitation 490 nm, emission 520 nm) or by fluorescence confocal microscopy. Internalized TM is indicated by the presence of bright green-yellow fluorescence in intracellular vesicles.

Another assay in which internalization can be observed also employs a HEC1-A cell line grown to confluent monolayers on permeable membrane supports (such as Costar, Cambridge, Mass., #3412). Cells are disrupted by trypsinization and the individual disrupted cells are collected by centrifugation. Cell pellets are washed twice with cold PBS. To perform the assay, 100 ng to 10 μg of a TM (e.g., fluorescein labeled) may be added to 1.5 mL of cell buffer and incubated with the cells at a temperature that allows binding and internalization of TMs, but that inhibits transcytosis (e.g., 90 minutes at 16° C.). The medium is then removed and the cells washed (e.g, twice at 4° C. with PBS). The cells are immersed in a fixation solution of, for example, 3% (w/v) paraformaldehyde, 1% (w/v) glutaraldehyde, 5% (w/v) sucrose, 100 mM Na phosphate pH 7.4 on ice for 30 minutes. The fixed cells may be placed on microscope slides and observed microscopically under epifluorescence illumination (excitation 490 nm, emission 520 nm) or by fluorescence confocal microscopy. Internalized TM is indicated by the presence of bright green-yellow fluorescence in intracellular vesicles.

Substitutions and modifications that result in a variant that retains the qualitative binding specificity for a basolateral factor and/or an NPE cell (i.e., a 3 to 1 or greater differential in signal intensity between basolateral and non-basolateral domains, or between epithelial and non-epithelial cells) are considered to be conservative. Preferred conservative substitutions and modifications include alterations in a sequence that render it, at least in part, consistent with the J chains of one or more other species. A TM may also, or alternatively, contain other sequences that confer properties not present in a native J chain. Other preferred modifications include the addition of one or more protein domains at the N- and/or C-terminus and/or altering the order of domains present within a native J chain sequence. A variant may contain any combination of such substitution(s) and/or modification(s), provided that the ability of the variant to specifically bind to an epithelial basolateral factor or to an NPE cell and cause internalization of the linked biological agent is not substantially reduced.

A native J chain typically has 6 domains. The first (N-terminal) domain is a short linear (i.e., as contrasted to a loop) peptide that serves (in vivo) as the junction between the signal peptide and the core TM molecule. Domain 1 typically contains 1–20 amino acid residues, and the first amino acid is generally D, E or Q. In FIG. 1, Domain 1 contains the amino acids up to and including residue number 11. Domain 1 is not essential for TM function, and variants that do not contain this domain are within the scope of the present invention.

Domain 2 typically contains 90 amino acids, and possesses substantial β-sheet character. This β-sheet region contains peptides of varying length lacking β-strand character (e.g., residues 26–31, 49–53), the peptides usually containing polar and/or charged amino acids. In a TM, Domain 2 is a covalently closed peptide loop, called the core, which is typically formed by an intramolecular cystine composed of the initial and ultimate residues of Domain 2 (residues 12 and 101 of FIG. 1). Within Domain 2, there may be another cystine bond that defines Domain 3, a peptide loop that is nested within the core. It has been found, within the context of the present invention, that the core (with or without Domain 3) is sufficient to provide TM function. Accordingly, a preferred TM contains Domain 2 (i.e., residues 12–70 and 92–101 of FIG. 1), or a portion or variant thereof that substantially retains TM function.

Within Domain 2, the second cysteine is generally separated from the initial cysteine of Domain 2 by a single amino acid residue (see, for instance, FIG. 1). Between the second and third cysteines of Domain 2 is a region of primarily β-sheet character. These two cysteines (2 and 3) when present, typically do not form cystines within the core. The fourth cysteine is typically separated from the third cysteine by two basic amino acid residues and initiates Domain 3. Domain 3 ends with the fifth cysteine which is oxidized by the fourth cysteine. The resulting cystine forms a covalent peptide loop defining Domain 3 contained completely within Domain 2. Cysteine 6 is the ultimate residue of Domain 2, and is oxidized to cystine by the initial residue of Domain 2.

Within the core is a canonical peptide sequence for N-linked glycosylation (e.g., NIS). When produced by eukaryotic cells, carbohydrate moieties can be covalently attached to an N residue of a TM at this site.

When present, Domain 3 is typically a peptide 21 amino acids in length. This domain is delimited by amino and carboxy terminal cysteine residues which form an intramolecular cystine bond that is contained completely within the core.

Domains 4–6 are carboxy terminal domains in native J chains which may, but need not, be present within a TM. Domain 4 is typically a peptide of seven amino acids. In native J chains, this peptide contains no cysteine residues and connects the core to Domain 5. Domain 5 is, when present, typically a peptide of 26 amino acids delimited by amino and carboxy terminal cysteine residues which form an intramolecular cystine bond resulting in a covalently closed loop. In native J chains, the amino and carboxy terminal portions of Domain 5 have substantial β-sheet character and are separated by a short 3–6 residue peptide with low β-sheet propensity. Domain 6 is typically a short peptide of five amino acids or less which serves as the carboxy terminus of a TM. Domains 4–6 are not essential for TM function.

As noted above, numerous variants of native J chain sequences may be employed within TMs as described herein. For example, a TM core, as described above, can serve as a molecular scaffolding for the attachment and/or substitution of Domains and/or additional molecular components. Possible variants include:

TMs in which Domain 1 comprises a peptide of about 13 amino acids, the middle third of which has substantial β-sheet character (e.g, DQEDERIVLVDNK; SEQ ID NO:37);

TMs in which the asparagine residue at position 48 is changed to histidine (e.g., AAT to CAC);

TMs in which Domain 1 comprises a three amino acid peptide DNK;

TMs in which Domain 1 contains a peptide with a sequence specific for recognition and cleavage by a protease which can be used to release distal portion of the TM from a proximal colinear peptide or protein (e.g., a peptide recognized by the tobacco etch virus protease Nia: ENLYFQS; SEQ ID NO:38);

TMs in which Domain 1 contains a peptide sequence which specifies the intracellular targeting of the contiguous peptide (e.g., a nuclear targeting peptide);

TMs in which one or both of the native cysteine residues 2 or 3 within Domain 2 are removed or replaced to eliminate the possibility of intermolecular crosslinking (e.g., substitutions of S, T, A, V or M residues for the native C);

TMs in which a portion of Domain 3 is deleted, such that there is a peptide bond between the amino acid distal to the end of the third β-sheet of Domain 3 and the initial residue of the ultimate peptide of Domain 3;

TMs in which other peptides that form loop structures or other antiparallel peptide domains are included in place of Domain 3, or between its defining cysteines, to provide functionalities or recognition domains to the TM (e.g., viral capsid protein loops);

TMs in which Domain 4 is truncated to form a TM without Domains 5 and 6;

TMs in which Domain 4 is replaced as described above for Domain 3 to introduce a new functionality, specificity and/or structure to the TM;

TMs in which Domain 4 contains a proteolytic site specific for a cellular compartment which would result in cleavage of the TM into two molecules in a cellular compartment;

TMs in which the loop structure of Domain 5 is replaced with a peptide sequence to provide functionalities or recognition domains to the TM (e.g., single chain antibody variable region or viral capsid protein loop);

TMs in which Domain 6 is terminated in a peptide sequence or is replaced with a peptide sequence that would target the contiguous TM protein to an intracellular target (e.g., KDEL, SEQ ID NO:44, or HDEL, SEQ ID NO:102, for retention in the endomembrane system);

TMs that additionally comprise one or more immunoglobulin-derived sequences (e.g., domains of the Ig heavy chain classes: alpha3, alpha2, alpha1, mu4, mu3, mu2, mu1) linked via one or more disulfide and/or peptide bonds. Such sequences may serve as attachment sites for one or more biological agents.

The above list of representative variants is provided solely for illustrative purposes. Those of ordinary skill in the art will recognize that the modifications recited above may be combined within a single TM and that many other variants may be employed in the context of the present invention.

TMs may generally be prepared using any of a variety of well known purification, chemical and/or recombinant methods. Naturally-occurring TMs (e.g., human J chain) may be purified from suitable biological materials, as described herein. All or part of a TM can be synthesized in living cells, with the sequence and content defined by the universal genetic code, a subset of the genetic code or a modified genetic code specific for the living cells. Any of a variety of expression vectors known to those of ordinary skill in the art may be employed to achieve expression in any appropriate host cell. Suitable host cells include insect cells, yeast cells, mammalian cells, plant cells, algae, bacteria and other animal cells (e.g., hybridoma, CHO, myeloma).

An example of a synthetic gene encoding a targeting molecule is provided in SEQ ID NO:7. Such synthetic genes may be ligated into, for example, a polyhedrin-based baculovirus transfer vector such as pMelBac A, pMelBac B or pMelBac C (Invitrogen, San Diego, Calif.) between suitable restriction sites (e.g., the BamHI and SalI sites) and introduced into insect cells such as High Five, Sf9 or Sf21 in a cotransfection event using Bac-N-Blu AcMNPV DNA (Invitrogen, San Diego, Calif.) according to standard methods. Other suitable vectors and host cells will be readily apparent to those of ordinary skill in the art.

Synthetic polypeptide TMs or portions thereof having fewer than about 100 amino acids, and generally fewer than about 50 amino acids, may be generated using synthetic techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is readily available from suppliers such as Applied BioSystems, Inc., Foster City, Calif., and may be operated according to the manufacturer's instructions.

In addition to the TMs described above, there are other molecules which may bind specifically to a basolateral factor associated with an epithelial cell and/or an NPE cell and subsequently result in internalization into epithelial cells followed by transcytosis through the epithelial barrier. Such molecules include peptides or proteins containing antibody domains which bind to the polyimmunoglobulin receptor. This type of molecule may be identified in screening assays employing epithelium-like surfaces in culture.

Within one suitable screening assay, a combinatorial library of peptides is employed, each peptide of which contains an easily identifiable biochemical or chemical marker such as a biotinyl-lysine residue, or a tyrosine residue modified by covalent linkage to radiolabeled iodine. In such an assay, individual peptides or families of peptides with 8 to 15 amino acid residues are incubated in solutions exposed to the basolateral domain of an epithelium-like monolayer cell culture and/or an NPE cell. After incubation of the peptide solution, the solution on the apical domain of the cell culture is assayed for the presence of transported peptides by analysis for the biochemical or chemical marker included during synthesis. Subsequent analysis of the peptide sequence of the transported peptide, for instance by mass spectrometry, is used to reveal the identity of a peptide which can be transported across an epithelium-like surfaces and/or NPE cell plasma membrane in culture. Any peptide identified in this manner is then synthesized by chemical means to contain a fluorescent marker. The peptide containing a fluorescent marker is then incubated in solutions exposed to the basolateral domain of an epithelium-like monolayer cell culture or NPE cells under conditions which allow binding, but not internalization (e.g., 4° C.) or under conditions which allow uptake but not transcytosis (e.g., 16° C.) and the cells observed microscopically to determine the ability of the peptides to bind or to be internalized by the cells of an epithelium-like layer.

A similar assay can be used to screen populations of monoclonal antibodies, single chain antibodies, antibody combining regions, or Fab fragments for the ability to bind to, be internalized and transcytosed by epithelial cells containing the polyimmunoglobulin receptor. Antibodies raised in animals immunized with secretory component, with the polyimmunoglobulin receptor, or animals naive to such immunization are incubated in solutions exposed to the basolateral domain of an epithelium-like monolayer cell culture or NPE cell. After incubation of antibodies, the solution on the apical domain of the cell culture is assayed for the presence of transported antibodies by analysis for the presence of antibody or antibody fragment. This evaluation can be performed using commercially available antibodies for enzyme linked immunosorbent assays, or by immunoblotting techniques. Either of these assays can be performed easily by one skilled in the art of characterizing antibodies.

Any antibody or antibody fragment identified in this manner may then be isolated and conjugated to a fluorescent marker. The immunoglobulin thus attached to a fluorescent marker is then incubated in solutions exposed to the basolateral domain of an epithelium-like monolayer cell culture under conditions which allow binding, but not internalization (e.g., 4° C.) or under conditions which allow uptake but not transcytosis (e.g., 16° C.) and the cells observed microscopically to determine the ability the antibodies to bind or to be internalized by the cells of an epithelium-like layer.

Ferkol et al., *J. Clin. Invest.* 92: 2394–2400 have identified an antibody binding domain by similar methods.

Linkage of a TM to one or more biological agents may be achieved by any means known to those in the art, such as genetic fusion, covalent chemical attachment, noncovalent attachment (e.g., adsorption) or a combination of such means. Selection of a method for linking a TM to a biological agent will vary depending, in part, on the chemical nature of the agent and depending on whether the agent is to function at the basolateral domain, within the epithelial cell, or undergo transcytosis. Linkage by genetic fusion may be performed using standard recombinant DNA techniques to generate a nucleic acid molecule that encodes a single fusion peptide containing both the biological agent(s) and the TM. Optionally, the fusion peptide may contain one or more linker sequences and/or sequences for intracellular targeting (e.g., KDEL, protease cleavage sites, nuclear targeting sequences, etc.). The recombinant nucleic acid molecule is then introduced into an appropriate vector and expressed in suitable host cells. Techniques for generating such a recombinant molecule and expressing a fusion peptide are well known to those of ordinary skill in the art (see, e.g., Sambrook et al., *Molecular Cloning: A Laboratory Manual*, 2d ed., Cold Spring Harbor Laboratory, Cold Spring Harbor, N.Y., 1989). Any biological agent having a known polypeptide sequence may be linked to a TM by genetic fusion. For example, using recombinant techniques, one or more immunoglobulin-derived sequences (e.g., single chain antigen binding proteins, hinge, Fv gamma or Fv kappa) may be linked to a TM at the N- and/or C-terminus.

Linkage may also be achieved by covalent attachment, using any of a variety of appropriate methods. For example, the TM and biological agent(s) may be linked using bifunctional reagents (linkers) that are capable of reacting with both the TM and the biological agent(s) and forming a bridge between the two. Commonly available bifunctional cross-linkers are capable of joining carbohydrates, amines, sulfhydryls and carboxyl functional groups, or may employ photoreactive groups to enable covalent linkage. These reagents are particularly useful for the attachment of, for example, additional peptide linkers that are in turn attached to biological agents. Covalent attachment of linkers may be accomplished through bonding to amino acid side chains present in the antigen combining site of an antibody linked to a TM. Briefly, attachment of linkers to such residues can occur as a result of the antibody recognition process itself when the linker is recognized as antigen and compatible reactive residues are present on the linker and in the binding domain of the antibody. Such reactive antibodies typically have antigen combining sites containing amino acid residues with side chains which can act as nucleophiles (e.g., aspartate, glutamate, glutamine, lysine and/or asparagine). For delivery of agents that will remain within the epithelial cell, linkers that are cleaved within the target cell may be particularly useful. Release of the biological agent within the cell may introduce or augment a genetic capability of the cell (e.g., increasing the P53 protein level in carcinoma cells) or may inhibit an existing cellular activity (e.g., antisense oligonucleotides may bind functional intracellular transcripts that are essential for tumorigenesis, tumor maintenance and/or metastases, such as transcripts that generate high levels of glycolytic enzymes).

Any of a variety of molecules may serve as linkers within the present invention. Polynucleotide and/or peptide linkers may be used. Such molecules may then be digested by, for example, intestinal nucleases and proteases (e.g., enterokinase, trypsin) respectively to release the biological agent. Preferred linkers include substrates for proteases associated with an epithelial barrier (i.e., proteases resident in, on or adjacent to epithelial cells or surfaces).

Numerous proteases are present in or associated with epithelial cells. Processing of secreted proteins, for example, requires proteolytic scission of a portion of the newly synthesized protein (referred to as the pre-protein) prior to secretion from the cellular endomembrane system. Further processing, which may be required to liberate an active enzyme from the cell, for example, can result from additional proteolysis wherein the substrate may be referred to as the pro-protein or pro-enzyme. The specific proteolytic cleavage sites of these pro-proteins can be identified by comparison of the amino acid sequence of the final secreted protein with the sequence of the newly synthesized protein. These cleavage sites identify the substrate recognition sequences of particular intracellular proteases. One such protease recognition site, specific to epithelial cells, is the amino acid sequence from residues 585–600 of the human polyimmunoglobulin receptor (pIgR, SEQ ID NO:45; numbering according to Piskurich et al., *J. Immunol.* 154:1735–1747, 1995). Another such protease recognition site, which identifies proteases abundant in cancer cells, comprises residues 30–40 of procathepsin E (SEQ ID NO:39). Since cancer cells secrete abundant quantities of proteases, the intracellular proteases which are responsible for their processing are also in abundance.

These protease recognition sites are extremely useful in the design of scissile linkers enabling the delivery of drugs, imaging compounds, or other biological agents to the intracellular environment of epithelial cells or to the epithelial barrier in general. Delivery of such compounds to epithelial cells can be accomplished by using residues 585–600 of human pIgR (SEQ ID NO:45) as part of the scissile linker joining the biological compound to TM. Delivery of anticancer drugs to tumors of epithelial origin can be accomplished using residues 30–40 of procathepsin E (SEQ ID NO:39) as part of the scissile linker to TM. Alternatively, scissile linkers may be designed from other cancer cell specific or epithelial barrier specific processing proteases which may be identified by the comparison of newly synthesized and secreted proteins or similar techniques. Other types of proteases that can be used to cleave scissile bonds can be found in the mammalian duodenum, for example. The enterokinase recognition sequence, $(Asp)_4$-lys, can be used as a scissile linker for delivery of biological compounds to the duodenum by TM mediated transcytosis across the duodenum epithelial barrier. Proteolytic cleavage releases the biological agent with a small fragment of linker (e.g., VQYT, SEQ ID NO:40, from procathepsin or EKVAD, SEQ ID NO:41, from pIgR). Such residual linker segments may in turn be further digested by proteolytic enzymes (e.g., carboxypeptidase II) to yield an unmodified biological agent.

Scissile peptide linkers are generally from about 5 to about 50 amino acid residues in length. They can be covalently linked to TM or to adducts attached to TM by genetic fusion techniques (i.e., in frame with the 5' or 3' sequence of TM codons or adduct codons) or by any of a variety of chemical procedures enabling the joining of various functional groups (e.g., $NH_2$, COOH, SH).

Other substrates for intracellular proteases associated with epithelial cells include, but are not limited to, substrates for a phospholipase or glycosidase. Alternatively, a linker may comprise repeating positively charged lysine residues that will bind negatively charged nucleic acid molecules for release in the cell. Peptide linkers may be particularly useful for peptide biological agents, such as the antibiotic cecropins, magainins and mastoparins.

Carbohydrates may be covalently attached to native carbohydrate or to the polypeptide backbone of a TM, and employed as linkers. Suitable carbohydrates include, but are not limited to, lactose (which may degraded by a lactase residing in, for example, the small intestine), sucrose (digested by a sucrase) and α-limit dextrin digested by a dextrinase). Enzymes responsible for cleaving carbohydrate linkers can be found attached to the brush border membranes of the luminal domain of the epithelial barrier. Sucrase-isomaltase, for example, will cleave 1,4-α bonds of maltose, maltotriose and maltopentose. An intestinal brush border specific linker would therefore be comprised of any polymer of maltose linked by 1,4-α bonds. When attached to TM, the linker would pass through the epithelial barrier by transcytosis and would only be cleaved by sucrase-isomaltase resident on the apical domain of the epithelial barrier.

Lipids may also, or alternatively, be covalently attached to the polypeptide backbone for use as linkers. A monoglyceride employed in this manner may then be digested by intestinal lipase to release a biological agent linked to glycerol or a fatty acid. Phospholipids may be attached to a TM via a peptide linkage to the phosphatidylserine polar head group or by an ether or ester linkage to one of the hydroxyl groups of the head group of phosphatidyl inositol. The non-polar head group (diacylglycerol) may be substituted entirely by the biological agent in active or inactive form. For example, a penicillin linked via its R group to the phosphate of 1-phospho-myo-inositol-TM will be inactive until released by a phospholipase C derived from a bacterial infection. Other suitable linker moieties will be apparent to those of ordinary skill in the art.

Linkage may also be performed by forming a covalent bond directly between a TM and a biological agent. Regardless of whether a linker is employed, any of a variety of standard methods may be used to form a covalent linkage. For peptide biological agents and linkers, such a covalent bond may be a disulfide bond between cysteine residues of the TM and biological agent. Briefly, such bonds may be formed during the process of secretion from the endomembrane system of higher organisms. In such cases, the peptide biological agent(s) and TM must contain appropriate signals specifying synthesis on endomembranes. Such signals are well known to those of ordinary skill in the art. Reactive antibodies may covalently attach directly to a biological agent or a linker. Antibodies raised against antigens containing reactive groups or transition state analogs for specific reactions may contain residues in the combining site capable of forming covalent interactions with the antigen or with similar molecules. An example of such a reaction occurs between a lysine residue in the combining site of the monoclonal antibody 38C2 which reacts to form a vinylogous amide linkage with diketone and other closely related molecules (Wagner et al., *Science* 270:1797–1800, 1995). A TM containing a reactive antibody or the combining site of a reactive antibody can be used to form covalent bonds with linkers of lipid, peptide, carbohydrate, nucleic acid or other compositions. TMs containing biological agents attached to TM via covalent bonds in the combining site can be expected to have normal conformations and functions in the antibody domain. The absence of modifications to antibody structure outside the antigen combining site minimize the potential for altering the recognition of such molecules as foreign when introduced into the body. Further, the molecules tethered through combining sites of antibodies of human origin are expected to have half-lives in serum and other body compartments similar to those of native antibodies and have a low propensity to stimulate antibody responses against the TM.

As noted above, any therapeutic biological agent may be linked to a TM. Biological agents include, but are not limited to, proteins, peptides and amino acids; nucleic acids and polynucleotides; steroids; vitamins; polysaccharides; minerals; fats; inorganic compounds and cells or cell components. A biological agent may also be a prodrug that generates an agent having a biological activity in vivo. In general, biological agents may be attached using a variety of techniques as described above, and may be present in any orientation.

The category of peptide biological agents includes a variety of binding agents. As used herein, a "binding agent" is any compound that binds to a molecule within the cell and inactivates and/or facilitates removal of the molecule. Binding agents include single chain antigen binding proteins, which may be used, for example, to inhibit viral pathogen assembly by binding essential components inside the cell and subsequently transcytosing components across the apical boundary; to bind and remove bacterial toxins by transcytosis; to bind and remove serum or cellular toxins or metabolites; or to bind and remove environmental toxins.

A binding agent may also be an antigen combining site such as, but not limited to, a reactive antigen combining site. For example, an antigen combining site may bind to an enzyme (e.g., an active site), and inhibit an activity of the enzyme. An antigen combining site may also bind to other molecules and inhibit other cellular functions such as, for example, a ribosome or transporter.

Enzymes may also be employed, including kinases, transferases, hydrolases, isomerases, proteases, ligases and oxidoreductases such as esterases, phosphatases, glycosidases and peptidases. For example, an enzyme linked to a TM could result in specific proteolytic cleavage of bacterial toxins, attachment proteins or essential cell surface functions (viral or bacterial), proteolytic cleavage of secreted cancer cell specific proteins (such as proteases) that are essential for tumor maintenance or metastases, degradation of cell surface carbohydrates essential to pathogenicity of viruses or bacteria or specific transfer of biochemical functions (such as phosphorylation) to inhibit extracellular cancer cell specific or pathogen specific functions.

Peptide biological agents may also be enzyme inhibitors (e.g., leupeptin, chymostatin or pepstatin); hormones (e.g., insulin, proinsulin, glucagon, parathyroid hormone, colony stimulating factor, growth hormone, thyroid hormone, erythropoetin, follicle stimulating hormone, luteinizing hormone, tumor necrosis factors); hormone releasing hormones (e.g., growth hormone releasing hormone, corticotropin releasing factor, luteinizing hormone releasing hormone, growth hormone release inhibiting hormone (somatostatin), chorionic gonadotropin releasing factor and thyroid releasing hormone); cell receptors (e.g., hormone receptors such as estrogen receptor) and cell receptor subunits; growth factors (e.g., tumor angiogenesis factor, epidermal growth factor, nerve growth factor, insulin-like growth factor); cytokines (e.g., interferons and interleukins); histocompatibility antigens; cell adhesion molecules; neuropeptides; neurotransmitters such as acetylcholine; lipoproteins such as alpha-lipoprotein; proteoglycans such as hyaluronic acid; glycoproteins such as gonadotropin hormone; antibodies (polyclonal, monoclonal or fragment); as well as analogs and chemically modified derivatives of any of the above.

Polynucleotide biological agents include antisense oligonucleotides (DNA or RNA) such as HIV, EBV EBNa-1 or reverse transcriptase antisense nucleotides; polynucleotides directed against active oncogenes or viral-specific gene products and polynucleotides complementary to unique sequences in the autoimmune B-cell immunoglobulin genes or T-cell receptor genes, or to mutant protein alleles (e.g., the mutant β-amyloid protein); and polynucleotides encoding proteins (e.g., DNA within expression vectors or RNA) including drug resistance genes. Also included are polynucleotide agents with catalytic activities (e.g., ribozymes) or with the ability to covalently bind to cellular or viral DNA, RNA or proteins. Nucleotides (e.g., thymine) and radionuclides (e.g., iodine, bromine, lead, palladium, copper) may also be employed.

A wide variety of steroid biological agents may be employed, including progesterone, androgens and estrogens (including contraceptives such as ethinyl estradiol). Similarly, agents such as vitamins (including fat soluble vitamins such as vitamins A, D, E and K and analogs thereof) may be linked to a TM. Inorganic biological agents include oxides, such as iron oxide. Polysaccharide biological agents include any of a variety of carbohydrates, as well as lipopolysaccharides and compounds such as heparin.

Within certain preferred embodiments, a biological agent linked to a TM induces death of NPE cells. Any of a wide variety of such lethal biological agents may be used for this purpose, and the efficacy is generally enhanced by TM-mediated delivery to NPE cells. For example, biological agents may be anti-tumor agents (e.g., doxorubcin, carboplatin, dactinomycin, fluorouracil or mitomycin), anti-metastatic cell agents (e.g., tamoxifen, etoposide, decarbazine, chlorambucil or cyclophosphamide) or an anti-endometriotic cell agent. In addition, killing of NPE cells by other biological agents, without regard to their mode of action, can be accomplished by enzymes and toxins which would otherwise be far too toxic in the absence of targeted delivery to NPE cells. For example, toxic enzymes such as saporin, as well as toxins such as ricin, may be linked to a TM and used for therapeutic purposes. Other suitable biological agents include antibodies, nucleic acids and carbohydrates.

Of course, the above examples of biological agents are provided solely for illustrative purposes and are not intended to limit the scope of the invention. Other agents that may be employed within the context of the present invention will be apparent to those having ordinary skill in the art.

In one embodiment, a targeting molecule as described above is linked to a biological agent that is not naturally associated with the targeting molecule. Within the context of this embodiment, the biological agent is not iodine. The biological agent may, for example, be an enzyme, binding agent, inhibitor, nucleic acid, carbohydrate or lipid. In one preferred embodiment the biological agent comprises an antigen combining site.

TMs linked to one or more biological agents may be employed whenever it is advantageous to deliver a biological agent to epithelial tissue or NPE cells (for internalization and/or transcytosis). For example, a variety of conditions associated with an epithelial surface or NPE cells may be treated and/or prevented using lethal or nonlethal biological agents linked to TMs. In general, such treatment employing a lethal biological agent will result in the death of an NPE cell. Cell death can be the direct result of contacting an NPE cell with the TM-biological agent or an indirect result mediated by other molecules. For example, direct cell killing could result from uptake of a TM-toxin (e.g., TM-doxorubicin or TM-saporin). Indirect killing could result from uptake of a TM-enzyme which then converts a prodrug to an active toxin (see, e.g., Table 1 in Deonarian and Epenetos, *Br. J. Cancer* 70:786–94, 1994). Such conditions include, but are not limited to, cancer, viral infection, and inflammatory disorders. Appropriate biological agents will vary depending on the nature of the condition to be treated and/or prevented and include those provided above, as well as others known to those of ordinary skill in the art.

As used herein, "treatment" refers to a lessening of symptoms or a delay in, or cessation of, the progression of the condition. A biological agent linked to a TM is generally administered to a patient afflicted with the condition in the form of a pharmaceutical composition, at a therapeutically effective dosage. To prepare a pharmaceutical composition, an effective concentration of one or more TM-biological agent complexes is mixed with a suitable pharmaceutical carrier or vehicle. Alternatively, a pharmaceutical composition may contain cells from the host or from another organism (e.g., a myeloma cell, stem cell, dendritic cell, hepatocyte or basal cell) which, when introduced into the body of the host, produce a TM. An amount of a TM (or cells that produce a TM in vivo) that, upon administration, ameliorates the symptoms or treats the disease is considered effective. Therapeutically effective concentrations and amounts may be determined empirically by testing the TMs in known in vitro and in vivo systems; dosages for humans or other animals may then be extrapolated therefrom. Pharmaceutical carriers or vehicles include any such carriers known to those skilled in the art to be suitable for the particular mode of administration.

The compositions of the present invention may be prepared for administration by a variety of different routes, including orally, parenterally, intravenously, intradermally, subcutaneously or topically, in liquid, semi-liquid or solid form and are formulated in a manner suitable for each route of administration. Preferred modes of administration depend upon the indication treated.

Solutions or suspensions used for oral, parenteral, intradermal, subcutaneous or topical application can include one or more of the following components: a sterile diluent, saline solution (e.g., phosphate buffered saline), fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. In addition, other pharmaceutically active ingredients and/or suitable excipients such as salts, buffers, stabilizers and the like may, but need not, be present within the composition. Liposomal suspensions may also be suitable as pharmaceutically acceptable carriers. These may be prepared according to methods known to those skilled in the art.

A TM may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others.

A pharmaceutical composition is generally formulated and administered to exert a therapeutically useful effect while minimizing undesirable side effects. The number and degree of acceptable side effects depends upon the condition for which the composition is administered. For example, certain toxic and undesirable side effects are tolerated when treating life-threatening illnesses, such as tumors, that would not be tolerated when treating disorders of lesser consequence. The concentration of biological agent in the composition will depend on absorption, inactivation and excretion rates thereof, the dosage schedule and the amount administered, as well as other factors known to those of skill in the art.

The composition may be administered one time, or may be divided into a number of smaller doses to be administered at intervals of time. The precise dosage and duration of treatment is a function of the disease being treated and may be determined empirically using known testing protocols or by extrapolation from in vivo or in vitro test data. Dosages may also vary with the severity of the condition to be alleviated. For any particular subject, specific dosage regimens may be adjusted over time according to the individual need of the patient.

The following Examples are offered by way of illustration and not by way of limitation.

EXAMPLES

Example 1

Preparation of Targeting Molecules

This Example illustrates the preparation of representative targeting molecules.

A. Purification of Representative TMs from Biological Sources

Preparation of dimeric IgA (dIgA). Ten ml of human IgA myeloma plasma (International Enzymes, Inc.; Fallbrook, Calif.) is mixed with an equal volume of PBS, and 20 ml of saturated ammonium sulfate (in $H_2O$) is added dropwise with stirring. After overnight incubation at 4° C., the precipitate is pelleted by centrifugation at 17,000×g for 15 minutes, and the supernatant fraction is discarded. The pellet is resuspended in 2 ml PBS. The resulting fraction is clarified by centrifigation at 13,500×g for 5 minutes and passage through a 0.45 $\mu$m filter (Nylon 66, 13 mm diameter, Micron Separations, Inc., Westborough, Mass.). Two ml (about half) of the clarified fraction is applied to a Sephacryl® S-200 column (1.6×51 cm; 0.25 ml/min PBS+ 0.1% sodium azide) (Pharmacia, Piscataway, N.J.), and 2 ml fractions are collected. Those fractions found to have the highest concentrations of dIgA (by SDS-PAGE analysis of 10 $\mu$l of each fraction) are lyophilized, resuspended in 200 $\mu$l deionized $H_2O$, and applied to a Superose® 6 column (1.0×30 cm; 0.25 ml/min PBS+0.1% sodium azide) (Pharmacia, Piscataway, N.J.). One ml fractions are collected and analyzed by SDS-PAGE. Fraction 13 is found to contain dIgA at over 90% purity.

Preparation of J chain by mild reduction of dIgA. A 1 ml sample containing less than 10 mg of dIgA is prepared as described above and dialyzed against buffer containing 100 mM sodium phosphate pH 6.0 and 5 mM EDTA. Six mg 2-mercaptoethylamine HCl are added to yield a final concentration of 0.05M, and the sample is incubated at 37° C. for 90 minutes. The reduced protein is passed over a desalting column equilibrated in PBS+1 mM EDTA. The protein-containing fractions are detected by assay with BCA reagent. J chain is then further purified by gel filtration and ion exchange chromatography.

Preparation of secretory IgA (sIgA). One hundred ml of human breast milk (Lee Scientific, Inc.; St. Louis, Mo.) is mixed with 100 ml PBS and centrifuged at 17,000×g for 1 hour at 4° C. The clear layer below the fat is transferred to clean centrifuge bottles and centrifuged at 17,000×g for 30 minutes at 4° C. The pH of the sample is adjusted to 4.2 with 2% acetic acid. After incubation at 4° C. for 1 hour, the sample is centrifuged at 17,000×g for 1 hour at 4° C., and the supernatant fraction is transferred to new tubes and adjusted to pH 7 with 0.1M NaOH. An equal volume of saturated ammonium sulfate is added, with stirring, and the sample is incubated at 4° C. overnight. The precipitated material is pelleted by centrifugation (17,000×g, 90 minutes, 4° C.), resuspended in approximately 7 ml PBS, and dialyzed extensively against PBS at 4° C.

Of the resulting approximately 25 ml, 1.1 ml is further purified. Undissolved solids are removed by centrifugation (13,500×g, 10 minutes) and an equal volume of 0.05 M $ZnSO_4$ is added to the clarified supernatant fraction. The pH is adjusted to 6.85 by addition of approximately 40 μl 1 M NaOH. After allowing the material to sit for 5 minutes at room temperature, the sample is centrifuged at 13,500×g for 10 minutes at room temperature. One and a half ml of the supernatant is mixed with 1.5 ml of saturated ammonium sulfate and allowed to stand at 4° C. for 1 hour. Precipitating material is pelleted by centrifugation (13,500×g, 10 minutes, room temperature) and is found to be greater than 90% sIgA by SDS-PAGE analysis.

Preparation of a molecule consisting of nicked J-chain crosslinked to two alpha-chain-derived peptides (CNBr cleavage fragment). A pellet containing sIgA prepared as described above ("Preparation of sIgA") is resuspended in 375 μl deionized $H_2O$. The sample is transferred to a glass vial and the vial is filled almost to the rim with 875 μl formic acid. Approximately 20 mg solid CNBr is added and a Teflon septum is used to seal the vial. The reaction is allowed to proceed at 4° C. overnight. The sample is then dialyzed against deionized $H_2O$ (two changes) and against PBS at 4° C., and lyophilized, resuspended with 200 μl $H_2O$, and applied to a Superose® 6 column (1.0×30 cm, 0.25 ml/min PBS+0.1% sodium azide). One ml fractions are collected. The fractions containing J chain are identified by immunoblotting of SDS-PAGE-separated proteins from aliquots of each fraction.

The fraction with the highest concentration of J chain is passed through a PD-10 column (Pharmacia, Uppsala, Sweden) equilibrated in 50 mM Tris-CL pH 8.1, and applied to a 20 PI Poros anion exchange column (4.6 mm×100 mm; PerSeptive Biosystems, Inc., Framingham, Mass.). The column is washed with 10 ml of 50 mM Tris-Cl pH 8.1, and eluted with a linear 0–1.0 M NaCl gradient in 50 mM Tris-Cl pH 8.1 (15 ml gradient). Elution of proteins from the column is monitored as absorbance at 280 nm and the J chain-containing fractions are identified by immunoblotting of SDS-PAGE-separated aliquots.

Alternative Methods for J Chain Purification. A variety of sources are suitable as starting material for isolation of human J chain. Polymeric IgA from sera of patients with IgA multiple myeloma, secretory IgA or IgM from sera of patients with Waldenstroms macroglobulinemia, as well as secretory IgA from human breast milk can be used as starting material for purification of J chain. Although the differences in the molecular weights of J chain (16,000) and L chains (22,500) should be large enough to allow satisfactory separation of these two chains by gel filtration, the unique conformation of J chain and its ability to dimerize often results in co-elution of J chain with L chain. Isolation procedures take advantage of J chain's negative charge (due to the high content of aspartic and glutamic acid residue) further increased by S-sulfitolysis or alkylation of reduced cysteine residues with iodoacetic acid. J chain can be subsequently separated from H and L chains by DEAE- or CM-cellulose chromatography using a linear salt gradient or by preparative electrophoresis in the presence or absence of dissociating agents.

Purification on DEAE-cellulose, which results in the isolation of immunochemically and physicochemically homogeneous J chain. As a starting material, the J chain-containing L chain fraction of polymeric IgA, S-IgA, or IgM, obtained by partial oxidative sulfitolysis and subsequent gel filtration on Sephadex® G-200 in 5 M guanidine-HCl can be used. Alternatively, S-sulfonated IgA or S-IGA can be directly applied on DEAE-cellulose. However, it is usually necessary to perform an additional separation using gel filtration on Sephadex® G-200 in 5 M guanidine-HCl to remove contaminating H chains.

Starting materials consist of the following reagents: L chain fraction of serum polymeric IgA or IgM, or colostral S-IgA; 0.01 M disodium phosphate in deionized 8 M urea solution and the same buffer with 0.7 M NaCl; DEAE-cellulose equilibrated in 0.01 M disodium phosphate containing 8 M urea; Sephadex® G-25 column in 1% $NH_4HCO_3$ solution.

Lyophilized L chain fraction is dissolved in 0.01 M disodium phosphate in 8 M urea, and applied on a DEAE-cellulose column equilibrated in the same phosphate solution. The column is thoroughly washed with this buffer. Absorbed proteins are eluted with a linear gradient of 0.01 M disodium phosphate in 8 M urea and 0.01 M disodium phosphate with 0.7 M NaCl. Two fractions are obtained, the later fraction containing J chain.

The J chain-containing fraction is desalted on a Sephadex® G-25 column in 1% $NH_4HCO_3$ adjusted to neutrality by bubbling with $CO_2$. The purity of J chain can be assessed by alkaline-urea gel-electrophoresis or immunoelectrophoresis with anti- L, H, and J chain reagents.

B. Direct Synthesis of TM Polypeptides

Manual syntheses are performed with BOC-L-amino acids purchased from Biosearch-Milligen (Bedford, Mass.). Machine-assisted syntheses are performed with BOC-L-amino acids from Peptide Institute (Osaka, Japan) and Peptides International (Louisville, Ky.). BOC-D-amino acids are from Peptide Institute. BOC-L-His(DNP) and BOC-L-Aba are from Bachem Bioscience (Philadelphia, Pa). Boc-amino acid-(4-carboxamidomethyl)-benzyl-ester-copoly(styrene-divinylbenzene)resins [Boc-amino acid-OCH2-Pam-resins] are obtained from Applied Biosystems (Foster City, Calif.) and 4-methylbenzhydrylamine (4MeBHA) resin is from Peninsula Laboratories, Inc. (Belmont, Calif.). Diisopropylcarbodiimide (DIC) is from Aldrich, and 2-(IH-benzotriazol-t-yl)-1,1,3,3-tetramethyluroniumhexafluorophosphate (HBTU) is obtained from Richelieu Biotechnologies (Quebec, Canada). For manual syntheses NN-diisopropylethylamine (DIEA), NN-dimethylformamide (DMF), dichloromethane (DCM) (all peptide synthesis grade) and 1-hydroxybenzotriazole (HOBT) are purchased from Auspep (Melbourne, Australia). For machine-assisted syntheses, DIEA and DCM are from ABI, and DMF is from Auspep. Trifluoroacetic acid (TFA) is from Halocarbon (New Jersey). Acetonitrile (HPLC grade) is obtained from Waters Millipore (Milford, Mass.). HF is purchased from Mallinckrodt (St. Louis, Mo.). Other reagents and solvents are ACS analytical reagent grade. Screw-cap glass peptide synthesis reaction vessels (20 mL) with a # 2 sintered glass filter frit are obtained from Embel Scientific Glassware (Queensland, Australia). A shaker for manual solid phase peptide synthesis is obtained from Milligen (Bedford, Mass.). An all-Kel F apparatus (Toho; from Peptide Institute, Osaka) is used for HF cleavage. Argon, helium and nitrogen (all ultrapure grade) are from Parsons (San Diego, calif.).

Chain assembly. Syntheses are carried out on Boc-amino acid-OCH2-Pam-resins, or on 4-MeBHA-resin. Boc amino acids are used with the following side chain protection: Arg(Tos); Asp(OBzl) (manual synthesis) and Asp(OcHxl); Cys(Bzl) (machine-assisted synthesis); Asn, unprotected (manual synthesis) and Asn(Xan) (machine-assisted synthesis); Glu(OcHxl); His(DNP); Lys(2ClZ); Thr(Bzl); Trp(InFormyl); and Tyr(BrZ). Gln and Met are used side chain unprotected.

Manual protocol. Syntheses are carried out on a 0.2 mmol scale. The $N^a$-Boc group is removed by treatment with 100% TFA for 2×1 minute followed by a 30 second flow with DMF. Boc amino acids (0.8 mmol) are coupled, without prior neutralization of the peptide-resin salt, as active esters preformed in DMF with either HOBt/DIC (30 minute activation), or HBTU/DIEA (2 minute activation) as activating agents. For couplings with active esters formed by HOBt/DIC, neutralization is performed in situ by adding 1.5 equivalents of DIEA relative to the amount of TFA $O^-.^+NH3$-peptide-resin salt to the activated Boc-amino acid/resin mixture. For couplings with active esters formed from HBTU/DIEA, an additional 2 equivalents DIEA relative to the amount of TFA $O^-.^+NH3$-peptide-resin salt are added to the activation mixture.

Coupling times are 10 minutes throughout without any double coupling. Samples (3–5 mg) of peptide-resin are removed after the coupling step for determination of residual free oc-amnino groups by the quantitative ninhydrin method. Coupling yields are typically >99.9%. All operations are performed manually in a 20 mL glass reaction vessel with a Teflon-lined screw cap. The peptide-resin is agitated by gentle inversion on a shaker during the NII-deprotection and coupling steps.

Deprotection and cleavage. His(DNP)-containing peptides are treated with a solution of 20% mercaptoethanol/10% DIEA in DMF for 2×30 minutes in order to remove the DNP group, prior to the removal of the Boc group. The $N^a$-Boc group is removed from the peptide-resin by treatment with neat TFA (2×1 minute). The peptide-resin is washed with DMF and neutralized with 10% DIEA in DMF (1×1 minute). After removal of the DNP and Boc group, the peptide-resin is treated with a solution of ethanolamine in water/DMF for 2×30 minutes to remove the formyl group of Trp(InFormyl).

The partially-deprotected peptide-resin is dried under reduced pressure after washing with DMF and DCM. Side chain protecting groups are removed and simultaneously the peptide is cleaved from the resin by treatment with HF/p-cresol (9:1 v/v, 0° C., 1 hour) or HF/p-cresol/thiocresol (9:0.5:0.5 by vol., 0° C., 1 hour). The HF is removed under reduced pressure at 0° C. and the crude peptide precipitated and washed with ice-cold diethyl ether, then dissolved in either 20% or 50% aqueous acetic acid, diluted with $H_2O$ and lyophilized.

Peptide joining. Joining of peptide segments of TM produced by the synthetic procedures described above is carried out by chemical ligation of unprotected peptides. These procedures can yield a free sulfhydryl at the junctional peptide bond or can yield a disulfide bond. Alternatively, cysteine residues at specified positions are replaced by L-aminobutyric acid.

In one procedure, the synthetic segment peptide 1, which contains a thioester at the α-carboxyl group, undergoes nucleophilic attack by the side chain of the Cys residue at the amino terminal of peptide 2. The initial thioester ligation product undergoes rapid intramolecular reaction because of the favorable geometric arrangement (involving a five-membered ring) of the α-amino group of peptide 2, to yield a product with the native peptide bond of a cysteine moiety at the ligation site. Both reacting peptide segments are in completely unprotected form, and the target peptide is obtained in final form without further manipulation. Additional cysteine residues in either peptide 1 or peptide 2 are left in their reduced state.

In another procedure, unprotected peptide segments containing terminal cysteine moieties are ligated via nucleophilic attack of a deprotonated α-thioacid group on a bromoacetyl moiety to form two monomers each with a short N- or C-terminal extension containing an unprotected sulfhydryl group. After derivatization of the cysteamine-containing monomer with 2,2'-dipyridyl disulfide, the desired disulfide linked heterodimer is formed by thiolysis of the S-(2-pyridyisulfenyl)cysteamine derivative.

These procedures are used to derive a variety of TM configurations, such as the representative TMs provided below:

TABLE I

Direct Synthesis of TM Polypeptides

| Segments | Chemistry | Strategy to form Closed Covalent Loop | Representative Attachment Sites |
|---|---|---|---|
| A. TM Core | | | |
| 1. 12–71 | N-cysteine C-glyNH$_2$CH$_2$CH$_2$SH | 71 to 91 via disulfide linker; | sulfhydryls at 14 and 68 |
| 2. 91–101 | N-glyCOCH$_2$SH C-cysteine | 12 to 101 via renaturation and oxidation to disulfide | |
| B. TM Core | | | |
| 1. 31–71 | N-BrCH$_2$CO C-glyNH$_2$CH$_2$CH$_2$SH | 71 to 91 via disulfide linker; | sulfhydryls at 14 and 68 |
| 2. 91–30 | N-glyCOCH$_2$SH | 30 to 31 via thioester; 12 to 101 exists as peptide bonds (serine-glycine-alanine in place of cys to cys disulfide) | |
| C. TM Extended | | | |
| 1. 1–67 | N-NH$^{3+}$ C-thioester | 67 to 68 via native chemical ligation; 118 to 119 via thio-ester; 71 to 91, 12 to 101 and 108 to 133 via renaturation and oxidation to form disulfides | sulfhydryls at 14 and 68 |
| 2. 68–118 | N-cysteine C-thioacid | | |
| D. TM Core Variations | | | |
| 1. serine 68 serine 14 | same as A or B " | Same as A or " | sulfydryl at 14; sulfhydryl at 68; free amines or free carboxyls |
| 2. serine 68 + serine 14 | serine " | " | |
| E. TM Extended Variations | | | |
| 1. 1–70 | N-NH$^{3+}$ C-thioester | 67 to 68 via native chemical ligation; 118 to 119 via thioester; 71 to 91, 12 to 101 and 108 to 133 via renaturation and oxidation | reactive group at 136 for attachment of bromo-acetylated peptide linker |
| 71–118 | N-cysteine C-thioacid | | |
| 119–136 | N-BrCH$_2$CO C-glyNH$_2$CH$_2$CH$_2$SH | | |

TABLE I-continued

Direct Synthesis of TM Polypeptides

| Segments | Chemistry | Strategy to form Closed Covalent Loop | Representative Attachment Sites |
|---|---|---|---|
| | | to form disulfides; serines at 14 and 68 | |
| 2. 1–70 | N-BrCH$_2$CO C-thioester | 67 to 68 via native chemical ligation; 118 to 119 via thioester; 71–91, 12 to 101 and 108 to 133 via renaturation and oxidation to form disulfides; serines at 14 and 68 | reactive group at 1 for attachment of sulfhydryl peptide linker |
| 71–118 | N-cysteine C-thioacid | | |
| 119–136 | N-BrCH$_2$CO C-COO$^-$ | | |

"Extended"=a TM comprising the 88 residues of the core, plus an additional 48 residues derived from native J chain; "Core"=residues 12–101 of native J chain; residues are indicated according to the numbering in FIG. 1

C. Synthesis and Expression of Synthetic DNAs Encoding TM

DNA chains can be synthesized by the phosphoramidite method, which is well known in the art, whereby individual building block nucleotides are assembled to create a desired sequence. Automated DNA synthesis of TM DNAs involves the synthesis and joining of individual oligonucleotides encoding portions of TMs to form the entire desired sequence. Synthetic DNA can be purchased from a number of commercial sources.

Transgenic expression of TMs requires ligation of the synthetic coding DNA into a vector for transformation of the appropriate organism. Techniques of ligation into vectors are well described in the literature. For example, in order to enable the introduction and expression of TMs in insect cells, the synthetic TM DNA is ligated into the pFastBac1 vector (GibcoBRL) to form the pFastBac1-TM recombinant. The recombinant vector is then used to transform *E. coli* bacteria containing a helper plasmid and a baculovirus shuttle vector. High molecular weight shuttle vector DNA containing transposed TM coding sequences is then isolated and used for transfection of insect cells. Recombinant baculovirus are harvested from transfected cells and used for subsequent infection of insect cell cultures for protein expression.

A TM can be synthesized by expressing in cells a DNA molecule encoding the TM. The DNA can be included in an extrachromosomal DNA element or integrated into the chromosomal DNA of the cell expressing the TM. Alternatively, the TM DNA can be included as part of the genome of a DNA or RNA virus which directs the expression of the TM in the cell in which it is resident. An example of a DNA sequence encoding TM is shown in SEQ ID NO:7. This DNA sequence and the amino acid sequence (SEQ ID NO:17) encoded by this TM DNA are also shown in Table II.

One method of synthesizing such a TM gene involves the sequential assembly of oligonucleotides encoding portions of the TM gene into a complete TM gene. The final assembly of the TM gene can occur in a DNA expression vector suitable for expression in a cellular system, or the TM gene can be constructed in a convenient cloning vector and subsequently moved into a DNA expression vector suitable for expression in a cellular system. An advantage of the sequential assembly of the TM gene from partial coding regions is the ability to generate modified versions of the TM gene by using alternative sequences for one or more of its individual portions during the assembly of the TM gene. Alternatively, the restriction endonuclease sites encoded in the TM gene can be used after the assembly of part or all of the TM gene to replace portions of the TM coding sequence to generate alternative TM coding sequences, using well known techniques, as described by Sambrook et al., *Molecular Cloning: A Laboratory Manual*, 2d ed., Cold Spring Harbor Laboratory, Cold Spring Harbor, N.Y., 1989. The TM gene can be divided into several partial coding regions: D1 encoding amino acids approximately −2 to 20; C2 encoding amino acids approximately 19 to 66; L3 encoding amino acids approximately 65 to 102; and T4 encoding amino acids approximately 102 to 142 of the sequence recited in Table II. Unless otherwise indicated, references to amino acid residue numbers in the following section are to the residue indicated in Table II.

Assembly of a synthetic gene encoding TM Core polypeptide. A TM Core gene sequence may be defined by the combination of C2, D1.1 (a modified version of D1, and L3Δ (a modified version of L3). One version of TM Core may be generated from the oligonucleotides 1.1, 2.1, 3, 4, 5, 6, 7, 8, 9L3Δ and 10L3Δ (SEQ ID NOs:48, 49, 54–56, 58, 60, 61, 63, 64) listed in Table III and encodes a polypeptide of sequence:
DQKCKCARITSRIIRSSEDPNEDI-VERNIRIIVPLNNRENISDPTSPLRTRFVYHLS DLCK-KDEDSATETC (Table IX and SEQ ID NO:18). A gene containing D1.1, C2, and L3Δ or alternate coding sequences that differ only in conservative substitutions or modifications is a complete TM Core gene.

Assembly of C2. In one example, de novo synthesis of a TM gene (including the TM core) may be initiated by assembly of a partial gene, called C2, encoding amino acids 19–66 of the TM. The sequence of C2 DNA and the peptide sequence encoded by the C2 DNA are shown in Table IV and SEQ ID NOS:9 and 19. C2 is generated by annealing oligonucleotides 3, 4, 5, 6, 7 and 8 (SEQ ID NOS:54, 55, 56, 58, 60, and 61, respectively) of Table III into a DNA fragment encoding approximately 48 amino acids of the TM Core polypeptide. Oligonucleotide pairs 3&4, 5&6, and 7&8 are first annealed pairwise into overlapping DNA duplexes, and the 3 double stranded DNAs are then annealed together to form a double stranded DNA complex composed of the 6 individual oligonucleotides. Oligonucleotides 1 and 8 have overhanging unpaired ends compatible with the unpaired ends of DNA restricted with the enzymes Xba I and Bgl II, respectively. C2 is annealed into the vector pMelBac XP, at the Xba I and Bgl II restriction endonuclease sites of the multiple cloning region and the DNA fragments enzymatically ligated to form the vector pTMC (Method 1).

Method 1: Synthesis of C2 DNA from oligonucleotides and insertion into pMelBac XP to form pTMC. Individual oligonucleotides 3, 4, 5, 6, 7, and 8 (SEQ ID NOs:54–56, 58, 60, 61) are separately dissolved in TE buffer (Sambrook et al., *Molecular Cloning: A Laboratory Manual*, 2d ed., Cold Spring Harbor Laboratory, Cold Spring Harbor, N.Y., 1989) at a concentration of 1 mM (1 nanomole/microliter). Two nanomoles of each oligonucleotide are combined with the same amount of its pair (e.g., (3&4), (5&6) or (7&8)) in 10 $\mu L$ of annealing buffer (10 mM Tris pH 8.0, 100 mM NaCl, 1 mM EDTA) in a microcentrifuge tube, and the tubes immersed in 50 mL boiling water for 5 minutes. The entire boiling water bath, including microcentrifuge tubes, is then removed from the heat source and allowed to cool to room temperature (approximately 24 ° C.), allowing the oligonucleotides to form base-paired DNA duplexes. After incubating for 30 minutes at room temperature, 1 nanomole of each oligonucleotide pairs (e.g., (3&4), (5&6), and (7&8)) are combined in a single microcentrifuge tube. The tube containing these DNA duplexes is incubated at 55 ° C. for 15 minutes in a heating block, removed from the heating block and equilibrated to room temperature, allowing overlapping complementary regions of the DNA duplexes to anneal, forming a DNA duplex encoding the partial TM DNA C2.

One nanomole of the oligonucleotide duplex is then mixed with 0.1 picomole of pMelBac XP which has previously been restricted with endonucleases Xba I and Bgl II. pMelBac XP is a DNA vector for cloning and subsequent expression in insect cells of synthetic TM genes, derived from pMelBac B (Invitrogen, San Diego, Calif.). The sequence of the secretion signal and multiple cloning site is (SEQ ID NOS:42 and 43):

met lys phe leu val asn val ala leu val phe met val tyr atg aaa ttc tta gtc aac gtt gcc ctt ttt atg gtc gta tac ile ser tyr ile tyr ala asp pro ser ser ser ala att tct tac atc tat gcg gat ccg agc tcg agt gct cta ga tct gca gct ggt acc atg gaa ttc gaa gct tgg agt cga ctc tgc tga The mixture of vector DNA and synthetic gene fragment is then heated to 35° C. for 15 minutes, then 1/10 volume of Ligation Stock Buffer is added, DNA ligase is added and the reaction mixture incubated at 12° C. for 12 hours to ligate the phosphodiester bonds among oligonucleotides and vector DNA, as described in Sambrook et al., *Molecular Cloning: A Laboratory Manual*, 2d ed., Cold Spring Harbor Laboratory, Cold Spring Harbor, N.Y., 1989. DNA is then used for transfection of competent *E. coli* cells by standard methods (see Sambrook et al., supra). Plasmid DNA is isolated from these cells and is evaluated by restriction endonuclease digestion or DNA sequencing to evaluate the success of synthetic DNA assembly and cloning. The resulting plasmid, pTMC is then used as a framework for successive addition of synthetic TM sequences.

Assembly of D1.1 and insertion into the TM synthetic gene. A fragment of the TM DNA proximal to C2, called D1.1, encodes amino acids 9 to 20 of the TM. The DNA sequence and primary amino acid peptide sequence of D1.1 are shown in Table V and SEQ ID NOS:10 and 20. D1.1 encodes the proximal amino acids of the TM Core polypeptide (residues 12 to 20) as well as a short peptide of three amino acids which serve to join the TM Core with a leader peptide (appropriate for the expression system employed for synthesis of TM). D1.1 is generated by annealing oligonucleotides 1.1 and 2.1 (SEQ ID NOS:48 and 51, respectively) into a DNA duplex as described in Method 1. Oligonucleotides 1.1 and 2.1 have overhanging unpaired ends compatible with the unpaired ends of BamHI (or Bgl II) and Xba I, respectively. D1.1 is annealed into pTMC at the BamHI and Xba I restriction endonuclease sites of the multiple cloning region and the DNA fragments enzymatically ligated, in a manner similar to that described in Method 1 for pTMC, to form the vector pTMD1.1C.

Assembly of L3Δ and insertion into the TM synthetic gene. A fragment of the TM DNA distal to C2, called L3Δ, encodes a contiguous polypeptide of amino acids 66–70 and 92–101 of the TM provided in Table II. The DNA sequence and peptide sequence of L3 are shown in Table VI and SEQ ID NOS:11 and 21. L3Δ is generated by annealing oligonucleotides 9L3Δ and 10L3Δ (SEQ ID NOS:63 and 64, respectively) into a DNA duplex as described in Method 1 to generate the distal portion of the TM Core DNA encoding approximately 14 amino acids. Oligonucleotides 9L3Δ and 10L3Δ have overhanging unpaired ends compatible with the unpaired ends of Bgl II and EcoRI, respectively. L3Δ is ligated into the vector pTMD1.1C at the Bgl II and EcoRI restriction endonuclease sites and the DNA fragments enzymatically ligated, in a manner similar to that described in Method 1 for pTMC, to form the vector pTMCore.

A TM may also be synthesized as described above, except that L3 (discussed below) is used in place of L3Δ. The sequence of such a TM is provided in Table X and SEQ ID NO:13.

Assembly of a synthetic gene encoding a full length TM polypeptide. A full length TM gene sequence may be defined by the combination of D1, C2, L3 and T4. One example of a full length TM gene (SEQ ID NO:7) is generated from the oligonucleotides 1, 2, 3, 4, 5, 6, 7, 8, 9, 10, 11, 12, 13, 14, 15, and 16 (SEQ ID NOS:46, 47, 54–56, 58, 60–62, 73–79, respectively) listed in Table III. A gene containing D1, C2, L3, and T4 or coding sequences that differ only in conservative substitutions or modifications is a full length TM gene.

Assembly of D1 and insertion into the TM synthetic gene. A fragment of the TM DNA proximal to C2, called D1, encodes amino acids −2 to 20 of the TM. The DNA sequence and peptide sequence of D1 are shown in Table VI and SEQ ID NOS:15 and 25. D1 encodes the proximal amino acids of the TM Core polypeptide (residues 12 to 20) as well as a peptide of 13 amino acids which serves to join the TM Core with a leader peptide (appropriate for the expression system employed for synthesis of TM). D1 is generated by annealing oligonucleotides 1 and 2 (Table III). Oligonucleotides 1 and 2 have overhanging unpaired ends compatible with the unpaired ends of BamHI (or Bgl II) and Xba I, respectively. D1 is annealed into pTMC at the BamHI and Xba I restriction endonuclease sites of the multiple cloning region and the DNA fragments enzymatically ligated, in a manner similar to that described in Method 1 for pTMC, to form the vector pTMDC.

Assembly of L3 and insertion into the TM synthetic gene. A fragment of the TM DNA distal to C2, called L3, encodes amino acids 66–101 of TM. The DNA sequence and peptide sequence of L3 are shown in Table VII.A and SEQ ID NOS:14 and 24. L3 is generated by annealing oligonucleotides 9, 10, 11, and 12 (SEQ ID NOS:62, 73–75, respectively) (Table III) into a DNA duplex to generate the distal portion of the TM Core DNA encoding approximately 35 amino acids. Oligonucleotide pairs 9& 10 and 11 & 12 are first annealed together to form a double stranded DNA complex composed of the 4 individual oligonucleotides. Oligonucleotides 9 and 12 have overhanging unpaired ends compatible with the unpaired ends of Bgl II and Pst I, respectively. L3 is annealed into the vector pTMDC at the Bgl II and PstI restriction endonuclease sites and the DNA fragments enzymatically ligated, in a manner similar to that described in Method 1 for pTMC, to form the vector pTMDCL.

Assembly of T4 and insertion into the TM synthetic gene. A fragment of the TM DNA distal to L3, called T4, encodes amino acids 102–141 of the TM. The DNA sequence and peptide sequence of L4 are shown in Table VIII and SEQ ID NOS:12 and 22. L3 is generated by annealing oligonucleotides 13, 14, 15, and 16 (SEQ ID NOS:76–79, respectively)

(Table III) into a DNA fragment which is the distal portion of the full length TM DNA encoding approximately 36 amino acids. Oligonucleotide pairs 13&14 and 15&16 are first annealed pairwise into overlapping DNA duplexes, and the two double stranded DNAs are subsequently annealed together to form a double stranded DNA complex composed of the 4 individual oligonucleotides. Oligonucleotides 13 and 16 have overhanging unpaired ends compatible with the unpaired ends of Pst I and EcoRI, respectively. T4 is annealed into the vector pTMDCL at the Pst I and Eco RI restriction endonuclease sites and the DNA fragments enzymatically ligated, in a manner similar to that described in Method 1 for pTMC, to form the vector pTM.

Assembly of synthetic genes encoding modified TM polypeptides. Other versions of TM genes, in which the peptide sequence is altered from the full length TM or TM Core, can be synthesized by using alternative oligonucleotides to 1, 2, 3, 4, 5, 6, 7, 8, 9, 10, 11, 12, 13, 14, 15, or 16 (SEQ ID NOS:46, 47, 54–56, 58, 60–62, 73–79, respectively) listed in Table III. These alternative oligonucleotides can be employed during synthesis of a partial TM gene, or can be used to generate DNA fragments which can replace coding sequences in an assembled TM gene or TM gene fragment by removing DNA fragments with restriction endonucleases, and replacing the original sequence with an alternative coding sequence. In addition, DNA sequences encoding polypeptides unrelated to TM can be inserted into the TM coding sequences at various positions.

Assembly of a synthetic gene encoding an aglycosylated TM polypeptide. In one example oligonucleotides 5 and 6 are replaced during the assembly of C2 with oligonucleotides 5.1 dg and 6.1 dg (SEQ ID NOS:57 and 59) (Table III) to form a new fragment called C2Δglyco. This oligonucleotide substitution results in an altered C2 DNA sequence so that the asparagine encoded at residue 48 is changed to a histidine. With the exception of the oligonucleotides 5.1 dg and 6.1 dg, C2Δglyco is created in the same manner as C2. C2Δglyco can be used in the synthesis of a variety TM sequences in a manner similar to that described for TM Core and full length TM sequences.

Assembly of a synthetic gene encoding a TM polypeptide with a modified L3 domain. In another example, TM amino acid residues 71–91 are replaced with the three amino acid peptide: ser-asp-ile. In this example oligonucleotides 9.2Δ3 and 10.2Δ3 (SEQ ID NOS:67 and 68) (Table III) are first annealed into a DNA duplex and subsequently annealed into the vector pTMDC at the Bgl II and Eco RI restriction endonuclease sites. The annealed DNA fragments are then enzymatically ligated to form the vector pTMLΔ3.

Assembly of synthetic genes encoding a TM polypeptide with cysteine residue 68 replaced. In other examples, the oligonucleotide pairs 9.3Δ3ser&10.3Δ3ser (SEQ ID NOS:69 and 70) or 9.3Δ3val&10.3Δ3val (SEQ ID NOS:71 and 72) are annealed into DNA duplexes and digested with the enzyme ClaI and subsequently annealed into pTMLΔ3 which has been digested with restriction enzymes ClaI and PstI. These two oligonucleotide pairs, when inserted into pTM1Δ3, result in a TMΔ3 molecule with the cysteine at position 68 replaced by serine or valine, respectively.

Assembly of synthetic genes encoding a TM polypeptide with cysteine residue 14 replaced. In another example the oligonucleotide pairs 1.2ser&2.2ser (SEQ ID NOS:50 and 51) or 1.2val&2.2val (SEQ ID NOS:52 and 53) can be annealed to generate an alternative domain to D1 with the cysteine residue 14 replaced with serine or valine, respectively. These oligonucleotide pairs are then annealed, in the same manner as described above for D1, into pTMC at the BamHI and Xba I restriction endonuclease sites of the multiple cloning region and the DNA fragments enzymatically ligated to form alternatives to the vector pTMD1C.

Assembly of a synthetic gene encoding a TM core polypeptide containing an endomembrane retention signal. In a further example TM core is synthesized with the endomembrane retention signal KDEL (SEQ ID NO:44) as the carboxyterminal amino acid residues. In this example oligonucleotides 9L3ΔKDEL and 10L3ΔKDEL (SEQ ID NOS:65 and 66) are substituted for oligonucleotides 9L3Δ and 10L3Δ during synthesis of TM core described above to form the vector pTMLΔ3KDEL.

Assembly of a synthetic gene encoding a full length TM polypeptide containing an endomembrane retention signal. In another example TM is synthesized with the endomembrane retention signal KDEL (SEQ ID NO:44) as the carboxyterminal amino acid residues. In this example oligonucleotides 15KDEL and 16KDEL (SEQ ID NOS:80 and 81) are substituted for oligonucleotides 15 and 16 as described above for synthesis of T4. The substitution of these two oligonucleotides results in the formation of coding sequence T4KDEL which when substituted for T4 in the above described synthesis of pTM results in the formation of the vector pTMKDEL.

Assembly of a synthetic gene encoding a TM polypeptide containing an additional amino terminal sequence. In one example a TM gene is synthesized with the polyimmunoglobulin receptor sequence from residues 585–600 (AIQDPRLAEEKAVAD; SEQ ID NO:45) included as part of the amino terminal domain. The oligonucleotides P1 and P2 (SEQ ID NOS:82 and 83) encode this polyimmunoglobulin receptor sequence and amino acid residues of D1. P1 and P2 have overhanging unpaired ends compatible with the unpaired ends of Bam HI and XbaI, respectively. The oligonucleotides P1 and P2 are annealed into a DNA duplex which can be used in place of D1.1 or D1 in the synthesis of a TM expression vectors as described above.

Assembly of a synthetic gene encoding a TM polypeptide in which a component of TM is replaced by another peptide domain, TpS2. In this Example, a TM gene is synthesized with a peptide replacing TM Domains 4, 5 and 6. This peptide, referred to as TpS2, encodes an enterokinase cleavable peptide between the terminal residue of Domain 2 and the coding sequence for the trefoil peptide pS2 (as reported in Suemori et al., *Proc. Natl. Acad. Sci.* 88:11017–11021, 1991). The DNA sequence and peptide sequence of TpS2 are shown in Table XI and SEQ ID NOS:16 and 26. TpS2 is generated by annealing oligonucleotides Tp1, Tp2, Tp3, Tp4, Tp5 and Tp6 (SEQ ID NOS:84–89, respectively) (Table III) into a DNA fragment which encodes approximately 64 amino acids. Oligonucleotide pairs Tp1 & Tp2, Tp3 & Tp4 and Tp5 & Tp6 are first annealed pairwise into overlapping DNA duplexes, and the two double stranded DNAs are subsequently annealed together to form a double stranded DNA complex composed of the 6 individual oligonucleotides. Oligonucleotides Tp1 and Tp6 have overhanging unpaired ends compatible with the unpaired ends of PstI and EcoRI restriction sites, respectively. TpS2 is annealed into the vector pTMDCL at the PstI and EcoRI restriction endonuclease sites and the DNA fragments enzymatically ligated, in a manner similar to that described in Method 1 for pTMC, to form a vector pTMpSp2, which encodes a TM with the trefoil peptide pS2 included as a replacement for TM Domains 4, 5, and 6.

D. Isolation and Expression of cDNA Encoding Human J chain

Two human small intestine cDNA libraries (Clontech Laboratories, Palo Alto Calif.; cat #HL1133a and dHL1133b) are screened using a synthetic DNA complementary to the 5' end of the human J chain messenger RNA. The probes are labeled with [$^{32}$P] using polynucleotide kinase in standard reactions. The library screening is performed as described by the manufacturer (Clontech). Hybridization is carried out according to Church and Gilbert, *Proc. Natl. Acad. Sci. USA* 81:1991–1995, 1984. After autoradiography, positive plaques are isolated and the phage are disrupted by boiling for 10 minutes. The cDNA inserts are amplified by PCR in a total volume of 50 μL containing standard PCR buffer, 25 pmoles of primers complementary to the 5' and 3' ends of the human J chain cDNA, 200 μM of each dNTP, and 1.0 unit of Taq polymerase. The DNA is denatured for 3 minutes at 94° C. prior to 35 cycles of amplification. Each cycle consisted of 1 min at 94° C., 1 min at 62° C., and 1 min at 72° C. The PCR fragments are cloned into pUC19 and sequenced. Full length cDNA inserts are then subcloned into the appropriate insect expression vector (pMelBacXP) utilizing restriction sites placed in the two PCR primers.

TABLE II

DNA Sequence and Primary Amino Acid Structure of a Representative Full Length TM Molecule

```
-2  -1   1   2   3   4   5   6   7   8   9  10  11  12  13  14  15  16
asp gln glu asp glu arg ile val leu val asp asn lys cys lys cys ala arg
gat cag gaa gat gaa cgt att gtt ctg gtt gac aac aag tgc aag tgt gct cgt
cta gtc ctt cta ctt gca taa caa gac caa ctg ttg ttc acg ttc aca cga gca 17  18  19  20  21  22  23  24  25  26  27  28  29  30  31  32  33  34
ile thr ser arg ile ile arg ser ser glu asp pro asn glu asp ile val glu
att act tct aga atc atc cgt agc tca gag gac cca aat gaa gat ata gtc gaa
taa tga aga tct tag tag gca tcg agt ctc ctg ggt tta ctt cta tat cag ctt 35  36  37  38  39  40  41  42  43  44  45  46  47  48  49  50  51  52
arg asn ile arg ile ile val pro leu asn asn arg glu asn ile ser asp pro
cgt aac atc cgt atc atc gtc cca ctg aat aac cgg gag aat atc tca gat cct
gca ttg tag gca tag tag cag ggt gac tta ttg gcc ctc tta tag agt cta gga 53  54  55  56  57  58  59  60  61  62  63  64  65  66  67  68  69  70
thr ser pro leu arg thr arg phe val tyr his leu ser asp leu cys lys lys
aca agt ccg ttg cgc aca cgc ttc gta tac cac ctg tca gat ctg tgt aag aag
tgt tca ggc aac gcg tgt gcg aag cat atg gtg gac agt cta gac aca ttc ttc 71  72  73  74  75  76  77  78  79  80  81  82  83  84  85  86  87  88
cys asp pro thr glu val glu leu asp asn gln ile val thr ala thr gln ser
tgt gat cca aca gag gta gag ctg gac aat cag ata gtc act gcg act caa agc
aca cta ggt tgt ctc cat ctc gac ctg tta gtc tat cag tga cgc tga gtt tcg 89  90  91  92  93  94  95  96  97  99 100 101 102 103 104 109 110 111
asn ile cys asp glu asp ser ala thr glu thr cys ser thr tyr asp arg asn
aac att tgc gat gag gac agc gct aca gaa acc tgc agc acc tac gat agg aac
ttg taa acg cta ctc ctg tcg cga tgt ctt tgg acg tcg tgg atg cta tcc ttg 112 113 114 115 116 117 118 119 120 121 122 123 124 125 126 127 128 129
lys cys tyr thr ala val val pro leu val tyr gly gly glu thr lys met val
aaa tgc tac acg gcc gtg gtt ccg ctc gtg tat ggt gga gag aca aaa atg gtg
ttt acg atg tgc cgg cac caa ggc gag cac ata cca cct ctc tgt ttt tac cac 130 131 132 133 134 135 136 137 138 139 140 141
glu thr ala leu thr pro asp ala cys tyr pro asp OPA
gaa act gcc ctt acg ccc gat gca tgc tat ccg gac tga attc
ctt tga cgg gaa tgc ggg cta cgt acg ata ggc ctg act taag
```

TABLE III

Oligonucleotides for Construction of Representative Partial TM Genes

| OLIGO | SEQUENCE |
|---|---|
| 1: | gat cag gaa gat gaa cgt att gtt ctg gtt gac aac aag tgc aag tgt gct cgt att act t |
| 2: | cta gaa gta ata cga gca cac ttg cac ttg ttg tca acc aga aca ata cgt tca tct tcc t |
| 1.1: | gat cag aag tgc aag tgt gct cgt att act t |
| 2.1 | ct aga agt aat acg agc aca ctt gca ctt ct |
| 1.2ser: | gat cag gaa gat gaa cgt att gtt ctg gtt gac aac aag tgc aag tcc gct cgt att act t |

TABLE III-continued

Oligonucleotides for Construction of Representative Partial TM Genes

| OLIGO | SEQUENCE |
|---|---|
| 2.2ser: | cta gaa gta ata cga gcg gac ttg cac ttg ttg tca acc aga aca ata cgt tca tct tcc t |
| 1.2val: | gat cag gaa gat gaa cgt att gtt ctg gtt gac aac aag tgc aag gtt gct cgt att act t |
| 2.2val: | cta gaa gta ata cga gca acc ttg cac ttg ttg tca acc aga aca ata cgt tca tct tcc t |
| 3: | cta gaa tca tcc gta gct cag agg acc caa atg aag ata tag tcg aa |
| 4 | gat acg gat gtt acg ttc gac tat atc ttc att tgg gtc ctc tga gct acg gat gat t |
| 5: | cgt aac atc cgt atc atc gtc cca ctg aat aac cgg gag aat atc tca g |
| 5.1dg: | cgt aac atc cgt atc atc gtc cca ctg aat aac cgg gag cac atc tca g |
| 6: | acg gac ttg tag gat ctg aga tat tct ccc ggt tat tca gtg gga cga t |
| 6.1dg: | acg gac ttg tag gat ctg aga tgt gct ccc ggt tat tca gtg gga cga t |
| 7: | atc cta caa gtc cgt tgc gca cac gct tcg tat acc acc tgt ca |
| 8: | gat ctg aca ggt ggt ata cga agc gtg tgc gca |
| 9: | gat ctg tgt aag aag tgt gat cca aca gag gta gag ctg gac aat cag ata gtc act gca |
| 9L3Δ: | gat ctg tgt aag aag gat gag gac agc gct aca gaa acc tgc tg |
| 10L3Δ: | aat tca gca ggt ttc tgt agc gct gtc ctc atc ctt ctt aca ca |
| 9L3ΔKDEL: | gat ctg tgt aag aag gat gag gac agc gct aca gaa acc tgc tac gag aag gat gag ctg tg |
| 10L3ΔKDEL: | aat tca cag ctc atc ctt cgc gtc gca ggt ttc tgt agc gct gtc ctc atc ctt ctt aca ca |
| 9.2Δ3: | gat ctg tgt aag aag tct gat atc gat gaa gat tcc gct aca gaa acc tgc agc aca tg |
| 10.2Δ3: | aat tca tgt gct gca ggt ttc tgt agc gga atc ttc atc gat atc aga ctt ctt aca ca |
| 9.3Δ3/ser68: | gat ctg tct aag aag tct gat atc gat gaa gat tac aga ttc ttc aga cta tag cta ctt cta a |
| 10.3Δ3/ser68: | aat ctt cat cga tat cag act tct tag aca |
| 9.3Δ3/val68: | gat ctg gtt aag aag tct gat atc gat gaa gat tac caa ttc ttc aga cta tag cta ctt cta a |
| 10.3Δ3/val68: | aat ctt cat cga tat cag act tct taa cca |
| 10: | att gtc cag ctc tac ctc tgt tgg atc aca ctt ctt aca ca |
| 11: | act caa agc aac att tgc gat gag gac agc gct aca gaa acc tgc a |
| 12: | ggt ttc tgt agc gct ctg ctc atc gca aat gtt gct ttg agt cgc agt gac tat ctg |
| 13: | gc acc tac gat agg aac aaa tgc tac acg gcc gtg gtt ccg ctc gtg tat ggt gga gag |
| 14: | gag cgg aac cac ggc cgt gta gca ttt gtt cct atc gta ggt gct gca |
| 15: | aca aaa atg gtg gaa act gcc ctt acg ccc gat gca tgc tat |

TABLE III-continued

Oligonucleotides for Construction of Representative Partial TM Genes

| OLIGO | SEQUENCE |
|---|---|
| | ccg gac tg |
| 16: | aat tca gtc cgg ata gca tgc atc ggg cgt aag ggc agt ttc<br>cac cat ttt tgt ctc tcc acc ata cac |
| 15KDEL: | aca aaa atg gtg gaa act gcc ctt acg ccc gat gca tgc tat<br>ccg gac aag gat gaa ttg tg |
| 16KDEL: | aat tca caa ttc atc ctt gtc cgg ata gca tgc atc ggg cgt<br>aag ggc agt ttc cac cat ttt tgt ctc tcc acc ata cac |
| P1: | gat cag gtc gct gcc atc caa gac ccg agg ctg ttc gcc gaa<br>gag aag gcc gtc gct gac tcc aag tgc aag tgt gct cgt att<br>act t |
| P2: | ct aga agt aat acg agc aca ctt gca ctt gga gtc agc gac ggc<br>ctt ctc ttc ggc gaa cag cct cgg gtc ttg gat ggc agc gac ct |
| Tp1: | gc gat gac gac gat aag gcc caa acg gag acc tgt act gtt gcg cct cgt<br>gaa cgg caa aac tgc gga ttc ccg gaa |
| Tp2: | gtt ttg ccg ttc acg agg cgc aac agt aca ggt ctc cgt ttg ggc ctt<br>atc gtc gtc atc gct tca |
| Tp3: | gta aca ccc tct cag tgc gct aat aaa ggc tgc tgt ttt gat gac acg<br>gta cgg ggc gtt ccg tgg tgc ttc |
| Tp4: | gcc ccg tac cgt gtc atc aaa aca gca gcc ttt att agc gca ctg aga<br>ggg tgt tac ttc cgg gaa tcc gca |
| Tp5: | tac ccc aat aca att gac gtt ccg cct gaa gaa gag tgc gag ccg taa g |
| Tp6: | aattc tta cgg ctc gca ctc ttc ttc agg cgg caa gtc aat tgt att<br>ggg gta gaa gca cca cgg aac |

TABLE IV

Peptide and DNA sequence of Domain C2 of TM (TM aa residues 19–65)

```
 19  20  21  22  23  24  25  26  27  28  29  30  31  32  33  34  35  36
ser arg ile ile arg ser ser glu asp pro asn glu asp ile val glu arg asn
>>>>>>>>>>>>>>>>>>>>>> oligo #3 >>>>>>>>>>>>>>>>>>>>>>>>>>>>>>/>>>>>>>>>
 ct aga atc atc cgt agc tca gag gac cca aat gaa gat ata gtc gaa cgt aac
     t tag tag gca tcg agt ctc ctg ggt tta ctt cta tat cag ctt gca ttg
     <<<<<<<<<<<<<<<<<<<<<<<< oligo #4 <<<<<<<<<<<<<<<<<<<<<<<<<<<<<<<<

37  38  39  40  41  42  43  44  45  46  47  48  49  50  51  52  53  54
ile arg ile ile val pro leu asn asn arg glu asn ile ser asp pro thr ser
>>>>>>>>>>>>>>>> oligo #5 >>>>>>>>>>>>>>>>>>>>>>>>>>>>>>>/>>>>>>>>>>>
atc cgt atc atc gtc cca ctg aat aac cgg gag aat atc tca gat cct aca agt
tag gca tag tag cag ggt gac tta ttg gcc ctc tta tag agt cta gga tgt tca
<<<<<<<< oligo #6 <<<<<<<<<<<<<<<<<<<<<<<<<<<<<<<<<<<<<<<<<<<<<<<<<<<<<

55  56  57  58  59  60  61  62  63  64  65  66      amino acid number
pro leu arg thr arg phe val tyr his leu ser asp leu  amino acid
>>>>>>>>>> oligo #7 >>>>>>>>>>>>>>>>>>>>>>>>>>       coding strand oligo
ccg ttg cgc aca cgc ttc gta tac cac ctg tca          coding strand
ggc aac gcg tgt gcg aag cat atg gtg gac agt cta g    noncoding strand
<<<</<<<<<< oligo #8 <<<<<<<<<<<<<<<<<<<<<<<<<<<<<   noncoding strand oligo
```

TABLE V

DNA sequence and primary amino acid structure of
Domain D1.1 of TM (TM aa residues 9–20)

```
 9   10  11  12  13  14  15  16  17  18  19  20
asp gln lys cys lys cys ala arg ile thr ser arg
>>>>>>>>>>>>> oligo D1.1>>>>>>>>>>>>>>>>>>>>>>>>>
gat cag aag tgc aag tgt gct cgt att act t
    tc ttc acg ttc aca cga gca taa tga aga tc
    <<<<<<<<<<<<<< oligo D2.1<<<<<<<<<<<<<<<<<
```

TABLE VI

DNA sequence and primary amino acid structure of
Domain D1 of TM (TM aa residues -2–20)

```
-2  -1   1   2   3   4   5   6   7   8   9   10
asp gln glu asp glu arg ile val leu val asp asn
gat cag gaa gat gaa cgt att gtt ctg gtt gac aac
    tc ctt cta ctt gca taa caa gac caa ctg ttg 11  12  13  14  15  16  17  18  19  20
lys cys lys cys ala arg ile thr ser arg
aag tgc aag tgt gct cgt att act t
ttc acg ttc aca cga gca taa tga aga tc
```

TABLE VII

Peptide and DNA sequence of Domain L3Δ of
TM (TM aa residues 66–70 and 92–101)

```
66  67  68  69  70  92  93  94  95  96  97
asp leu cys lys lys asp glu asp ser ala thr
gat ctg tgt aag aag gat gaa gat tcc gct aca
    ac aca ttc ttc cta ctt ctc agg cga tgt 99  100 101
glu thr cys OPA
gaa acc tgc tg
ctt tgg acg act taa
```

TABLE VII.A

Peptide and DNA sequence of Domain L3 of TM
(TM aa residues 66–101)

```
66  67  68  69  70  71  72  73  74  75  76  77
asp leu cys lys lys cys asp pro thr glu val glu
gat ctg tgt aag aag tgt gat cca aca gag gta gag
cta gac aca ttc ttc aca cta ggt tgt ctc cat ctc 78  79  80  81  82  83  84  85  86  87  88  89
leu asp asn gln ile val thr ala thr gln ser asn
ctg gac aat cag ata gtc act gcg act caa agc aac
gac ctg tta gtc tat cag tga cgc tga gtt tcg ttg 90  91  92  93  94  95  96  97      100
ile cys asp glu asp ser ala thr glu thr cys
att tgc gat gag gac agc gct aca gaa acc tgc
taa acg cta ctc ctg tcg cga tgt ctt tgg acg
```

TABLE VIII

DNA and Primary Amino Acid Sequence of T4
Fragment (TM aa residues 102–141)

```
102 103 104 109 110 111 112 113 114 115 116
ser thr tyr asp arg asn lys cys tyr thr ala
    gc acc tac gat agg aac aaa tgc tac acg gcc
acg tcg tgg atg cta tcc ttg ttt acg atg tgc cgg
```

TABLE VIII-continued

DNA and Primary Amino Acid Sequence of T4
Fragment (TM aa residues 102–141)

```
117 118 119 120 121 122 123 124 125 126 127 128
val val pro leu val tyr gly gly glu thr lys met
gtg gtt ccg ctc gtg tat ggt gga gag aca aaa atg
cac caa ggc gag cac ata cca cct ctc tgt ttt tac 129 130 131 132 133 134 135 136 137 138 139 140
val glu thr ala leu thr pro asp ala cys tyr pro
gtg gaa act gcc ctt acg ccc gat gca tgc tac cct
cac ctt tga cgg gaa tgc ggg cta cgt acg atg gga 141
asp OPA
gac tg
ctg act taa
```

TABLE IX

DNA Sequence and Primary Amino Acid Sequence of a
Representative TM Core Element

```
 9   10  11  12  13  14  15  16  17  18  19  20
asp gln lys cys lys cys ala arg ile thr ser arg
gat cag aag tgc aag tgt gct cgt att act tct aga
cta gtc ttc acg ttc aca cga gca taa tga aga tct 21  22  23  24  25  26  27  28  29  30  31  32
ile ile arg ser ser glu asp pro asn glu asp ile
atc atc cgt agc tca gag gac cca aat gaa gat ata
tag tag gca tcg agt ctc ctg ggt tta ctt cta tat 33  34  35  36  37  38  39  40  41  42  43  44
val glu arg asn ile arg ile ile val pro leu asn
gtc gaa cgt aac atc cgt atc atc gtc cca ctg aat
cag ctt gca ttg tag gca tag tag cag ggt gac tta 45  46  47  48  49  50  51  52  53  54  55  56
asn arg glu asn ile ser asp pro thr ser pro leu
aac cgg gaa aat atc tca gat cct aca agt ccg ttg
ttg gcc ctt tta tag agt cta gga tgt tca ggc aac 57  58  59  60  61  62  63  64  65  66  67  68
arg thr arg phe val tyr his leu ser asp leu cys
cgc aca cgc ttc gta tac cac ctg tca gat ctg tgt
gcg tgt gcg aag cat atg gtg gac agt cta gac aca 69  70  92  93  94  95  96  97  99  100 101
lys lys asp glu asp ser ala thr glu thr cys
aag aag gat gag gac agc gct aca gaa acc tgc
ttc ttc cta ctc ctg tcg cga tgt ctt tgg acg OPA Eco RI
    tg
    act taa
```

TABLE X

DNA Sequence and Primary Amino Acid Structure of
a Representative TM

```
 9   10  11  12  13  14  15  16  17  18  19  20
asp gln lys cys lys cys ala arg ile thr ser arg
gat cag aag tgc aag tgt gct cgt att act tct aga
cta gtc ttc acg ttc aca cga gca taa tga aga tct 21  22  23  24  25  26  27  28  29  30  31  32
ile ile arg ser ser glu asp pro asn glu asp ile
atc atc cgt agc tca gag gac cca aat gaa gat ata
tag tag gca tcg agt ctc ctg ggt tta ctt cta tat 33  34  35  36  37  38  39  40  41  42  43  44
val glu arg asn ile arg ile ile val pro leu asn
```

TABLE X-continued

DNA Sequence and Primary Amino Acid Structure of a Representative TM

```
gtc gaa cgt aac atc cgt atc atc gtc cca ctg aat
cag ctt gca ttg tag gca tag tag cag ggt gac tta 45  46  47  48  49  50  51  52  53  54  55  56
asn arg glu asn ile ser asp pro thr ser pro leu
aac cgg gag aat atc tca gat cct aca agt ccg ttg
ttg gcc ctc tta tag agt cta gga tgt tca ggc aac 57  58  59  60  61  62  63  64  65  66  67  68
arg thr arg phe val tyr his leu ser asp leu cys
cgc aca cgc ttc gta tac cac ctg tca gat ctg tgt
gcg tgt gcg aag cat atg gtg gac agt cta gac aca 69  70  71  72  73  74  75  76  77  78  79  80
lys lys cys asp pro thr glu val glu leu asp asn
aag aag tgt gat cca aca gag gta gag ctg gac aat
ttc ttc aca cta ggt tgt ctc cat ctc gac ctg tta 81  82  83  84  85  86  87  88  89  90  91  92
gln ile val thr ala thr gln ser asn ile cys asp
cag ata gtc act gcg act caa agc aac att tgc gat
gtc tat cag tga cgc tga gtt tcg ttg taa acg cta 93  94  95  96  97  99 100 101 102
glu asp ser ala thr glu thr cys tyr OPA
gag gac agc gct aca gaa acc tgc tac tga attc
ctc ctg tcg cga tgt ctt tgg acg atg act
```

TABLE XI

DNA and Primary Amino Acid Sequence of TpS2

```
101 102
cys ser asp asp asp asp lys ala gln thr glu thr cys thr val ala pro
    gc  gat gac gac gat aag gcc caa acg gag acc tgt act gtt gcg cct
act tcg cta ctg ctg cta ttc cgg gtt tgc ctc tgg aca tga caa cgc gga arg glu arg gln asn cys gly phe pro gly val thr pro ser gln cys ala
cgt gaa cgg caa aac tgc gga ttc ccg gaa/gta aca ccc tct cag tgc gct
gca ctt gcc gtt ttg/acg cct aag ggc ctt cat tgt ggg aga gtc acg cga asn lys gly cys cys phe asp asp thr val arg gly val pro trp cys phe
aat aaa ggc tgc tgt ttt gat gac acg gta cgg ggc gtt ccg tgg tgc ttc/
tta ttt ccg acg aca aaa cta ctg tgc cat gcc ccg/caa ggc acc acg aag tyr pro asn thr ile asp val pro pro glu glu glu cys glu phe
tac ccc aat aca att gac gtt ccg cct gaa gaa gag tgc gag ccg taa g
atg ggg tta tgt taa ctg caa ggc gga ctt ctt ctc acg ctc ggc att cttaa
```

Example 2
Linkage of Biological Agents to a TM

This Example illustrates the attachment of representative biological agents to a TM.

A Preparation of Functional Genes Attached to TM

Preparation of TM-polylysine conjugates. TM isolated from biological sources as described above, is covalently linked to poly (L-lysine) (Mr 20,000 D) using the heterobifunctional crosslinking reagent N-succinimidyl 3-(2-pyridyldithio) proprionate (SPDP). The TM polypeptide is incubated with a fifteen fold molar excess of poly (L-lysine) and SPDP and the reaction is carried out at 2° C. for 24 hours. The conjugate is dialyzed to remove low molecular weight reaction products, and analyzed by separating the resultant proteins using 0.1% SDS-7.5% polyacrylamide gel electrophoresis.

Genes and plasmid preparation. The pRICIN, containing the ricin gene from *ricinus communis* (Shire et. al., *Gene* 93:183–188, 1990) ligated to the Rous sarcoma virus long terminal repeat promoter inserted into a modified pBR322 vector, is used for introduction of a lethal genetic function into NPE cells. The plasmids are grown in *E. coli* DH5α, extracted and purified by standard techniques. Digestions of the plasmids with restriction endonucleases yields the appropriate fragments, and purity is established by 1.0% agarose gel electrophoresis.

Preparation of TM-polylysine-DNA complexes. Complexes are formed by combining plasmid DNA with the TM-polylysine in 3M NaCl. The charge ratio of the DNA phosphate to lysine is ~1.2:1. Samples are incubated for 60 minutes at 22° C., then dialyzed against 0.15 NaCl for 16 hours through membranes with a 3,500-dalton molecular mass limit. The complexes are filtered through a Millipore filter with 15 μm pore size, and maintained at 4° C. prior to use. The final TM complex is referred to as TM-polylysine-DNA.

Determination of optimal conjugate to DNA proportion. To determine the optimal proportion of conjugate to DNA, increasing amounts of the conjugate are added to 10 μg of PRSVZ, producing 1:4, 1:8, 1:16, and 1:32 DNA to carrier (TM) molar ratios. Samples are incubated as described above, and dialyzed overnight against 0.15 M NaCl. The complexes are filtered before use. Samples containing equal amounts of DNA (1 μg) are separated by 1.0% agarose gel electrophoresis and stained with ethidium bromide. The plasmid DNA is transferred onto a nitrocellulose filter and analyzed by Southern blot hybridization, using the 2.3-kB EcoRI fragment of PRSVZ as a DNA probe.

B. Preparation of TM with various linkers to lethal agents.

Lethal agent attached to TM via a scissile peptide and a pH-sensitive hydrazide linker. 3-deamino-3-(4-morpholinyl)-doxorubicin (MRA) is prepared from doxorubicin (Aldrich, Milwaukee, Wis.) by reacting via dialdehyde, followed by a reaction with sodium cyanoborohydrate. MRA is purified after separation on a silica gel column, and is modified with a peptide spacer by the following procedure. First, the peptide KAHKVDMVQYT (SEQ ID NO:39) is esterified to yield the corresponding methyl ester. This is followed by condensation of the amino terminal of the peptide with succinic anhydride, followed by reaction of the ester terminal with hydrazine hydrate to yield the monohydrazide. The hydrazide moiety of this activated peptide is then reacted via the C-13 carbonyl group of MRA to yield MRA-KAHKVDMVQYT (SEQ ID NO:39), which is purified by preparative thin layer chromatography (TLC). The purified drug-linker intermediate is reacted at the succinic acid terminal with dicyclohexyl carbodiimide (DCC) and N-hydroxysuccinimide (NHS). This activated compound is again purified by TLC and then coupled to the lysine residues of TM by adding a 20-fold excess of MRA-KAHKVDMVQYT (SEQ ID NO:39) to purified TM at pH 8 for 3 hr. The TM used in this preparation is isolated from biological sources as described above. This conjugate is referred to as TM(bio)-MRA.

The conjugation reaction mixture is centrifuged to remove precipitated material and is applied to a column of Sephadex G-50 equilibrated with 50 mM sodium phosphate, 0.1 M NaCl (pH 7.0). The fractions containing TM(bio)-MRA conjugate are pooled and stored at 4° C. The drug-to-TM ratio is determined by spectrophotometry at 280 and 480 nm using extinction coefficients of 9.9 mM$^{-1}$ cm$^{-1}$ and 13 mM$^{-1}$ cm$^{-1}$, respectively. The conjugates are analyzed by HPLC on a Dupont GF-250 gel filtration column and by NaDodSO4/PAGE on 7.5% acrylamide gels under nonreducing conditions.

Lethal enzyme attached to TM. Saporin (Sigma, St. Louis, Mo.) is covalently linked to TM using sulfo-LC-SPDP according to the manufacturer's protocol (Pierce, Rockford, Ill.)

Lethal agent attached to dimeric IgA via a scissile peptide and a pH-sensitive hydrazide linker. The activated drug linker compound, prepared as described above, is coupled to the lysine residues of dimeric IgA by adding a 20-fold excess of MRA-KAHKVDMVQYT (SEQ ID NO:39) to purified dIgA at pH 8 for 3 hr. The dIgA used in this preparation is isolated from biological sources as described above. This conjugate is referred to as dIgA-MRA.

The conjugation reaction mixture is centrifuged to remove precipitated material and is applied to a column of Sephadex G-50 equilibrated with 50 mM sodium phosphate, 0.1 M NaCl (pH 7.0). The fractions containing dIgA-KAHKVDMVQYT-MRA (SEQ ID NO:39) conjugate are pooled and stored at 4° C. The drug-to-dIgA ratio is determined by spectrophotometry at 280 and 480 nm using extinction coefficients of 9.9 mM$^{-1}$ cm$^{-1}$ and 13 mM$^{-1}$ cm$^{-1}$, respectively. The conjugates are analyzed by HPLC on a Dupont GF-250 gel filtration column and by NaDodSO$_4$/PAGE on 7.5% acrylamide gels under nonreducing conditions.

Lethal agent targeted for retention in the endoplasmic reticulum. 3-deamino-3-(4-morpholinyl)-doxorubicin (MRA) is prepared from doxorubicin (Aldrich, Milwaukee, Wis.) by reacting via dialdehyde, followed by a reaction with sodium cyanoborohydrate. MRA is purified after separation on a silica gel column, and is modified with a peptide spacer by the following procedure. First, the peptide KAHKVDMVQYT (SEQ ID NO:39) is esterified to yield the corresponding methyl ester. This is followed by reaction of the ester terminal with hydrazine hydrate to yield the monohydrazide. The hydrazide moiety of this activated peptide is then reacted via the C-13 carbonyl group of MRA to yield MRA- KAHKVDMVQYT (SEQ ID NO:39), which is purified by preparative thin layer chromatography (TLC). The purified drug-linker intermediate is reacted at the amino terminal with SPDP. This activated compound is again purified by TLC and then coupled to the sulfhydryl groups of core TM by adding a 20-fold excess of MRA-KAHKVDMVQYT (SEQ ID NO:39) to purified TM at pH 8 for 3 hours. The TM used in this preparation is isolated from transgenic insect cells. The ER retention signal KDEL is synthesized as part of the TM core protein by phosphoramidite oligonucleotide coupling as described above and ligated into an insect expression vector to create pTM. This conjugate is referred to as TM(KDEL)-MRA.

The conjugation reaction mixture is centrifuged to remove precipitated material and is applied to a column of Sephadex G-50 equilibrated with 50 mM sodium phosphate, 0.1 M NaCl (pH 7.0). The fractions containing TM(KDEL)-MRA conjugate are pooled and stored at 4° C. The drug-to-TM ratio is determined by spectrophotometry at 280 and 480 nm using extinction coefficients of 9.9 mM$^{-1}$ cm$^{-1}$ and 13 mM$^{-1}$ cm$^{-1}$, respectively. The conjugates are analyzed by HPLC on a Dupont GF-250 gel filtration column and by NaDodSO$_4$/PAGE on 7.5% acrylamide gels under nonreducing conditions.

Lethal agent tethered to an antigen combining site. The linker peptide KAHKVDMVQYT (SEQ ID NO:39) is first coupled to MRA via the hydrazide as described above. The peptide-MRA is then coupled to diketone 1 (Wagner et al., *Science* 270:1797–1800, 1995) using EDC and sulfoNHS as described above. The 1,3-diketone 1 is synthesized as described in Wagner et al.

The diketone-peptide-MRA conjugate is reacted with the antigen combining site of antibody 38C2 (Wagner et al.) engineered to be covalently linked to TM. The engineering procedures to produce TM-38C2 are essentially as described above in example 2C. mRNA derived from a cell line producing 38C2 antibody is isolated by established procedures. Specific linkers are employed to prime polymerase chain reactions resulting in amplification of the Fv-Cγ1 section, and the entire kappa chain in separate amplification reactions as described above.

The resulting heavy chain (Fv-C$_H$1)-TM:kappa hybrid antibody joined by disulfide bridges through the constant regions of heavy and light chains is purified as described above.

Reaction of the hybrid antibody with the diketone-peptide-MRA results in a stable vinylogous amide linkage between the diketone moiety and the epsilon amino group of a lysine residue in the binding pocket. The final compound is referred to as TM(38C2)-MRA.

Example 3

Intracellular and Clinical Delivery of a Biological Agent

This Example illustrates the use of a TM prepared as described in Example 2 for delivery of biological agents to epithelial cells.

A. Cells and cultures.

Culture medium. The following stock solutions are combined to make the culture solution, referred to as MDCK medium. Mimimal essential medium (MEM) with Earle's balanced salt solution with 25 mM Hepes, 500 mL; 100× L-glutamine, 2.5 mL; 100× non-essential amino acids, 5.4 mL; fetal bovine serum, 27 mL; penicillin-streptomycin, 5.5 mL; 10 mg/mL gentamicin, 220 μL. All stock solutions are purchased from Gibco-BRL, Bethesda, Md.

Preparation of NPE cell cultures from epithelial cell monolayers. For experimental preparation of non-adherent epithelial cells containing no basalateral or apical domains, culture dishes were coated with a layer of agarose. Five ml of 1% agarose (melted and cooled to ~50° C.) was poured into a 75 cm$^2$ tissue culture flask and allowed to solidify. Confluent MDCK, HEC1A or HT-29 cells growing in a 75 cm$^2$ flask were washed twice with sterile PBS followed by two ml of a trypsin solution. Cells are incubated at 37° C. for 10 minutes. Nine ml of pre-warmed culture medium was added to the flask with swirling to suspend the cells. Cells were transferred to a sterile 50 ml conical tube and centrifuged at 300×g for 5 minutes. The supernatant was discarded and the cell pellet re-suspended in 20 ml of fresh culture medium. Two ml of the cell suspension was added to agarose coated flasks followed by an additional 10 ml of pre-warmed medium. The flasks were incubated in 5% $CO_2$ at 37° C. Cells are viable for at least one week.

Preparation of NPE cells from human pleural fluid. Pleural fluid was obtained from patients diagnosed with malignant pleural effusion. Cells contained in the fluid were obtained by low speed centrifugation as soon as possible after removal from the pleural cavity. The cell pellet was resuspended in MDCK culture medium. Cells are referred to as MPEs.

Cell Viability Assay. Live cells are distinguished by the presence of ubiquitous intracellular esterase activity, determined by the enzymatic conversion of the non-fluorescent cell permeable calcein AM to the intensely fluorescent calcein. Reagents (kit #L3224) were obtained from Molecular Probes, Inc. (Eugene, Oreg.). Cells were harvested by low speed centrifugation and washed three time with sterile PBS. Cells were stained in solution according to the instructions provided by the manufacturer. Cell viability, expressed in terms of percentage of cells producing calcein, was estimated by fluorescence microscopy.

Labelling NPE cells with Texas red-labelled dimeric IgA. Purified dimeric IgA(1–5 mg) was chilled in 0.1 M sodium carbonate/bicarbonate, pH 9.0 Fifty microliters of Texas red sulfonyl chloride (1 mg dissolved in 50 $\mu$l anhydrous acetonitrile) was added to the protein solution. The reaction is incubated at 25° C. for 1 hour. The reaction was passed over a desalting column to remove unconjugated dye. The absorbance ratio (520 nm/280 nm) of the desalted dIgA was 0.8.

Cells were collected by low speed centrifugation and resuspended in 1 ml cell culture medium. Cells were chilled to 4° C. Two hundred microliter aliquots of the cell suspension were placed in chilled 1.5 ml tubes. Ten microliters of Texas red-dIgA conjugate was added to each tube; binding was allowed to proceed overnight at 4° C. with shaking. One ml of chilled cell culture medium was added and the cells were recovered by centrifugation and resuspension in 50 ml of medium. Binding to Texas red-dIgA was visualized by fluorescence microscopy.

B. Delivery of Genes to NPE Cells Using TM-Polylysine

TM-polylysine-DNA delivery to NPE cells. Four days before transfection, the cells are washed twice with PBS, pH 7.4. Half of the cells are returned to RPMI Media 1640, and the remaining half are grown in Leibovitz L15 Media, a glucose-deficient culture medium. Human gamma interferon, 100 U/ml, is added to half of the cells grown in glucose-deficient media 2 days before transfection. Transfer of NPE cells to glucose-free media increases expression of pIgR, as does treatment with human gamma interferon. Cell density is approximately $5\times10^4$ cells per plate at the time of transfection. Growth medium is changed and the cells are washed with PBS. Solutions containing TM-polylysine-DNA complex (2.5 pmol DNA noncovalently bound to 10, 20, 40, or 80 pmol TM), polylysine-DNA complex (2.5 pmol DNA complexed with 1.2 nmol polylysine), TM-polylysine (80 pmol) alone, or 2.5 pmol (20 $\mu$g) DNA alone, are added to individual plates. Each sample is filtered prior to transfection of cells. After the cells are incubated for 48 hours at 37° C., either in vitro or in situ, viability assays are performed.

All NPE cells (MDCK, HT-29, HEC-1A, MPEs) transfected with TM-polylysine-DNA show a significantly reduced production of calcein as judged by the viability assay and fluorescence microscopy analysis. Viability is estimated to be less than 10% as a result of TM-polyline-DNA treatment. Cells are also incubated with Texas red-dIgA. Cells with reduced viability (no green fluorescence) are invariably red fluorescent due to dIgA binding, indicating that cell killing is due to TM delivery of the cytotoxic agent.

C. Delivery of Lethal Agents Attached to TM with Linkers

Delivery to NPE cells of a lethal agent linked to TM. NPE cells (MDCK, HT-29, HEC-1A, MPEs; $2\times10^6$ cells in 1 ml culture medium) prepared as described above, are incubated with TM(bio)-MRA (100 $\mu$l of 1 mg/ml in culture medium) for 2–12 hours at 37° C. Cells are then pelleted by low speed centrifugation, resuspended in culture medium and incubated at 37° C. for an additional 12–48 hours. Cells are then assayed for viability and Texas red-IgA as described above.

All NPE cells (MDCK, HT-29, HEC-1A, MPEs) incubated with TM(bio)-MRA show a significantly reduced production of calcein as judged by the viability assay and fluorescence microscopy analysis. Viability is estimated to be less than 10% as a result of TM(bio)-MRA exposure. Cells with reduced viability (no green fluorescence) are invariably red fluorescent due to dIgA binding, indicating that cell killing is due to TM delivery of the cytotoxic agent.

Delivery to NPE cells of a lethal enzyme linked to TM. NPE cells (MDCK, HT-29, HEC-1A, MPEs; $2\times10^6$ cells in 1 ml culture medium) prepared as described above, are incubated with TM-SAP (100 $\mu$l of 1 mg/ml in culture medium) for 2–12 hours at 37° C. Cells are then pelleted by low speed centrifugation, resuspended in culture medium and incubated at 37° C. for an additional 12–48 hours. Cells are then assayed for viability and Texas red-IgA as described above.

All NPE cells (MDCK, HT-29, HEC-1A, MPEs) incubated with TM-SAP show a significantly reduced production of calcein as judged by the viability assay and fluorescence microscopy analysis. Viability is estimated to be less than 10% as a result of TM-SAP exposure. Cells with reduced viability (no green fluorescence) are invariably red fluorescent due to dIgA binding, indicating that cell killing is due to TM delivery of the cytotoxic agent.

Delivery to NPE cells of a killing agent linked to dimeric IgA. NPE cells (MDCK, HT-29, HEC-1A, MPEs; $2\times10^6$ cells in 1 ml culture medium) prepared as described above, are incubated with dIgA-MRA (100 $\mu$l of 1 mg/ml in culture medium) for 2–12 hours at 37° C. Cells are then pelleted by low speed centrifugation, resuspended in culture medium and incubated at 37° C. for an additional 12–48 hours. Cells are then assayed for viability and Texas red-IgA as described above.

All NPE cells (MDCK, HT-29, HEC-1A, MPEs) incubated with dIgA-MRA show a significantly reduced production of calcein as judged by the viability assay and fluorescence microscopy analysis. Viability is estimated to be less than 10% as a result of dIgA-MRA exposure. Cells with reduced viability (no green fluorescence) are invariably red fluorescent due to dIgA binding, indicating that cell killing is due to TM delivery of the cytotoxic agent.

Delivery to NPE cells of a killing agent targeted for retention in the endoplasmic reticulum. NPE cells (MDCK, HT-29, HEC-1A, MPEs; $2\times10^6$ cells in 1 ml culture medium) prepared as described above, are incubated with TM(KDEL)-MRA (100 $\mu$l of 1 mg/ml in culture medium) for 2–12 hours at 37° C. Cells are then pelleted by low speed centrifugation, resuspended in culture medium and incubated at 37° C. for an additional 12–48 hours. Cells are then assayed for viability and Texas red-IgA as described above.

All NPE cells (MDCK, HT-29, HEC-1A, MPEs) incubated with TM(KDEL)-MRA show a significantly reduced production of calcein as judged by the viability assay and fluorescence microscopy analysis. Viability iss estimated to be less than 10% as a result of TM(KDEL)-MRA exposure. Cells with reduced viability (no green fluorescence) are invariably red fluorescent due to dIgA binding, indicating that cell killing is due to TM delivery of the cytotoxic agent.

Delivery to NPE cells of a killing agent linked to the antigen combining site of a hybrid antibody. NPE cells (MDCK, HT-29, HEC-1A, MPEs; 2×10$^6$ cells in 1 ml culture medium) prepared as described above, are incubated with TM(38C2)-MRA (100 μl of 1 mg/ml in culture medium) for 2–12 hours at 37° C. Cells are then pelleted by low speed centrifugation, resuspended in culture medium and incubated at 37° C. for an additional 12–48 hours. Cells are then assayed for viability and Texas red-IgA as described above.

All NPE cells (MDCK, HT-29, HEC-1A, MPEs) incubated with TM(38C2)-MRA show a significantly reduced production of calcein as judged by the viability assay and fluorescence microscopy analysis. Viability iss estimated to be less than 10% as a result of TM(38C2)-MRA exposure. Cells with reduced viability (no green fluorescence) are invariably red fluorescent due to dIgA binding, indicating that cell killing is due to TM delivery of the cytotoxic agent.

Clinical use of a killing agent linked to TM, Malignant pleural effusion is a disease which usually involves widespread metastases. Eighty percent of malignant pleural effusion are of epithelial cell origin. Patients with malignant pleural effusion present clinically with shortness of breath and heaviness in the chest; pleural fluid is frequently contaminated with NPE cells. Initial diagnosis of patients is by chest x-ray which shows the accumulation of pleural fluid, usually unilateral. Diagnosis is confirmed by cytologic examination of aspirated fluid (thoracentesis), or histologic examination of pleural biopsies. NPE cells obtained from pleural fluid are evaluated, as described above, for their susceptibility to lethal agents linked to TM.

Treatment protocols utilizing lethal agents linked to TM are intended to optimize NPE cell killing. Mesothelial cells lining the pleural cavity are unaffected by the TM conjugate since they contain no receptors for TM uptake. The drug is linked to TM via a peptide linker, KAHKVDMVQYT (SEQ ID NO:39), prepared as described above. Between 100 μg and 1 g of drug conjugate is injected intra-pleurally after removal of 50% of the effusion volume by needle aspiration. A #16 gauge needle with or without a polyethylene catheter is placed in the pleural space by intercostal access along the posterior axcillary line after local anesthesia with 2% lidocaine. One-half of the effusion (about 1 liter) is removed by vacuum aspiration, after which the pre-determined dose of drug conjugate is injected in diluted volume of 10–50 cc's of sterile saline. Following this, the patient is maneuvered in caudal, cephalade, and right and left lateral positions to enhance distribution. At select intervals, pleural fluid is aspirated to determine cell viability. This procedure is repeated at intervals determined by efficacy indices and patient tolerance to toxicity. Clinical efficacy is assessed by observing patient symptoms, physical signs, weight, and serial chest x-rays. The determination of the rate of re-accumulation or resolution of effusion is determined by serial x-rays. Cell viability is used to determine cytologic efficacy utilizing vital staining and immunologic techniques to assess cell function.

Patients treated with TM(bio)-MRA as described display a significant reduction in NPE cells occupying the pleural cavity after one month.

From the foregoing, it will be appreciated that, although specific embodiments of the invention have been described herein for the purpose of illustration, various modifications may be made without deviating from the spirit and scope of the invention.

Summary of Sequence Listing

SEQ ID NO:1 is amino acid sequence of human J chain
SEQ ID NO:2 is amino acid sequence of mouse J chain
SEQ ID NO:3 is amino acid sequence of rabbit J chain
SEQ ID NO:4 is amino acid sequence of bovine J chain
SEQ ID NO:5 is amino acid sequence of bull frog J chain
SEQ ID NO:6 is amino acid sequence of earth worm J chain
SEQ ID NO:7 is nucleotide sequence of "full length" TM cDNA (Table II)
SEQ ID NO:8 is nucleotide sequence of Core TM cDNA (Table IX)
SEQ ID NO:9 is nucleotide sequence of C2 fragment (Table IV)
SEQ ID NO:10 is nucleotide sequence of D1.1 fragment (Table V)
SEQ ID NO:11 is nucleotide sequence of L3D fragment (Table VII)
SEQ ID NO:12 is nucleotide sequence of T4 fragment (Table VIII)
SEQ ID NO:13 is nucleotide sequence of Core TM cDNA using L3 (Table X)
SEQ ID NO:14 is nucleotide sequence of L3 fragment (Table VII.A)
SEQ ID NO:15 is nucleotide sequence of D1 fragment (Table VI)
SEQ ID NO:16 is nucleotide sequence of TpS2 (Table XI)
SEQ ID NO:17 is amino acid sequence of "full length" TM cDNA (Table II)
SEQ ID NO:18 is amino acid sequence of Core TM cDNA (Table IX)
SEQ ID NO:19 is amino acid sequence of C2 fragment (Table IV)
SEQ ID NO:20 is amino acid sequence of D1.1 fragment (Table V)
SEQ ID NO:21 is amino acid sequence of L3D fragment (Table VII)
SEQ ID NO:22 is amino acid sequence of T4 fragment (Table VIII)
SEQ ID NO:23 is amino acid sequence of Core TM cDNA using L3 (Table X)
SEQ ID NO:24 is amino acid sequence of L3 fragment (Table VII.A)
SEQ ID NO:25 is amino acid sequence of D1 fragment (Table VI)
SEQ ID NO:26 is amino acid sequence of TpS2 (Table XI)
SEQ ID NO:27 is complementary nucleotide sequence of "full length" TM cDNA (Table II)
SEQ ID NO:28 is complementary nucleotide sequence of Core TM cDNA (Table IX)
SEQ ID NO:29 is complementary nucleotide sequence of C2 fragment (Table IV)
SEQ ID NO:30 is complementary nucleotide sequence of D1.1 fragment (Table V)
SEQ ID NO:31 is complementary nucleotide sequence of L3D fragment (Table VII)
SEQ ID NO:32 is complementary nucleotide sequence of T4 fragment (Table VIII)
SEQ ID NO:33 is complementary nucleotide sequence of Core TM cDNA using L3 (Table X)
SEQ ID NO:34 is complementary nucleotide sequence of L3 fragment (Table VII.A)
SEQ ID NO:35 is complementary nucleotide sequence of D1 fragment (Table VI)
SEQ ID NO:36 is complementary nucleotide sequence of TpS2 (Table XI)
SEQ ID NO:37 is Domain 1, 13 amino acid peptide with substantial β-sheet character SEQ ID NO:38 is peptide recognized by the tobacco etch virus protease Nia
SEQ ID NO:39 is amino acid residues from pro-cathepsin E
SEQ ID NO:40 is linker from procathepsin
SEQ ID NO:41 is linker from polyimmunoglobulin receptor
SEQ ID NO:42 is nucleotide sequence of secretion signal from pMelBac
SEQ ID NO:43 is amino acid sequence of secretion signal from pMelBac
SEQ ID NO:44 is endomembrane retention signal
SEQ ID NO:45 is residues 585–600 of polyimmunoglobulin receptor (human)
SEQ ID NO:46 is Oligonucleotide 1
SEQ ID NO:47 is Oligonucleotide 2
SEQ ID NO:48 is Oligonucleotide 1.1
SEQ ID NO:49 is Oligonucleotide 2.1
SEQ ID NO:50 is Oligonucleotide 1.2ser
SEQ ID NO:51 is Oligonucleotide 2.2ser
SEQ ID NO:52 is Oligonucleotide 1.2val
SEQ ID NO:53 is Oligonucleotide 2.2val
SEQ ID NO:54 is Oligonucleotide 3
SEQ ID NO:55 is Oligonucleotide 4
SEQ ID NO:56 is Oligonucleotide 5
SEQ ID NO:57 is Oligonucleotide 5.1 dg
SEQ ID NO:58 is Oligonucleotide 6
SEQ ID NO:59 is Oligonucleotide 6.1 dg
SEQ ID NO:60 is Oligonucleotide 7
SEQ ID NO:61 is Oligonucleotide 8
SEQ ID NO:62 is Oligonucleotide 9
SEQ ID NO:63 is Oligonucleotide 9L3Δ
SEQ ID NO:64 is Oligonucleotide 10L3Δ
SEQ ID NO:65 is Oligonucleotide 9L3ΔKDEL
SEQ ID NO:66 is Oligonucleotide 10L3ΔKDEL
SEQ ID NO:67 is Oligonucleotide 9.2Δ3
SEQ ID NO:68 is Oligonucleotide 10.2Δ3
SEQ ID NO:69 is Oligonucleotide 9.3Δ3/ser68
SEQ ID NO:70 is Oligonucleotide 10.3Δ3/ser68
SEQ ID NO:71 is Oligonucleotide 9.3Δ3/val68
SEQ ID NO:72 is Oligonucleotide 10.3Δ3/val68
SEQ ID NO:73 is Oligonucleotide 10
SEQ ID NO:74 is Oligonucleotide 11
SEQ ID NO:75 is Oligonucleotide 12
SEQ ID NO:76 is Oligonucleotide 13
SEQ ID NO:77 is Oligonucleotide 14
SEQ ID NO:78 is Oligonucleotide 15
SEQ ID NO:79 is Oligonucleotide 16
SEQ ID NO:80 is Oligonucleotide 15KDEL
SEQ ID NO:81 is Oligonucleotide 16KDEL
SEQ ID NO:82 is Oligonucleotide P1
SEQ ID NO:83 is Oligonucleotide P2
SEQ ID NO:84 is Oligonucleotide Tp1
SEQ ID NO:85 is Oligonucleotide Tp2
SEQ ID NO:86 is Oligonucleotide Tp3
SEQ ID NO:87 is Oligonucleotide Tp4
SEQ ID NO:88 is Oligonucleotide Tp5
SEQ ID NO:89 is Oligonucleotide Tp6

What is claimed is:

1. A targeting molecule linked to at least one biological agent, wherein said targeting molecule is a polypeptide that:
   (a) forms a closed covalent loop; and
   (b) contains at least three peptide domains having β-sheet character, each of the domains being separated by domains lacking β-sheet character;
   such that the targeting molecule linked to the biological agent is capable of entering and killing a non-polarized epithelial cells
   wherein the polypeptide is a J chain, or a portion thereof such that the ability of the portion to enter a non-polarized epithelial cell is not substantially reduced.

2. A targeting molecule linked to at least one biological agent, such that the targeting molecule linked to the biological agent is capable of entering and killing a non-polarized epithelial cell, wherein said targeting molecule is a polypeptide that:

(a) forms a closed covalent loop; and (b) contains at least three peptide domains having β-sheet character, each of the domains being separated by domains lacking β-sheet character;

wherein said targeting molecule is linked to at least one biological agent by a substrate for an intracellular or extracellular enzyme associated with or secreted from a non-polarized epithelial cell; and wherein the polypeptide is a J chain, or a portion thereof such that the ability of the portion to enter a non-polarized epithelial cell is not substantially reduced.

3. A targeting molecule according to claim 2, wherein said enzyme is selected from the group consisting of proteases, glycosidases, phospholipases, esterases, hydrolases, and nucleases.

* * * * *

UNITED STATES PATENT AND TRADEMARK OFFICE
CERTIFICATE OF CORRECTION

PATENT NO. : 6,251,392 B1
DATED : June 26, 2001
INVENTOR(S) : Mich B. Hein et al.

It is certified that error appears in the above-identified patent and that said Letters Patent is hereby corrected as shown below:

Column 87, claim 1,
Line 28, "epithelial cells" should read -- epithelial cell; --.

Signed and Sealed this

Fifteenth Day of January, 2002

Attest:

JAMES E. ROGAN
Attesting Officer       Director of the United States Patent and Trademark Office

UNITED STATES PATENT AND TRADEMARK OFFICE
CERTIFICATE OF CORRECTION

PATENT NO. : 6,251,392 B1
DATED : June 26, 2001
INVENTOR(S) : Hein et al.

It is certified that error appears in the above-identified patent and that said Letters Patent is hereby corrected as shown below:

<u>Title page,</u>
Item [73], correct name of Assignee to read -- Epicyte Pharmaceutical, Inc. -- in place and instead of "Epicyte Pharmaceuticals, Inc."

Signed and Sealed this

Seventeenth Day of June, 2003

JAMES E. ROGAN
*Director of the United States Patent and Trademark Office*